US012797148B2

(12) United States Patent
Liu

(10) Patent No.: US 12,797,148 B2
(45) Date of Patent: Nov. 17, 2026

(54) MECHANICAL ARM, MASTER OPERATING PLATFORM, AND SURGICAL ROBOT

(71) Applicant: SHENZHEN EDGE MEDICAL CO., LTD., Shenzhen (CN)

(72) Inventor: Fang Liu, Shenzhen (CN)

(73) Assignee: SHENZHEN EDGE MEDICAL CO., LTD., Shenzhen (CN)

( * ) Notice: Subject to any disclaimer, the term of this patent is extended or adjusted under 35 U.S.C. 154(b) by 232 days.

(21) Appl. No.: 18/702,495

(22) PCT Filed: Oct. 20, 2022

(86) PCT No.: PCT/CN2022/126409

§ 371 (c)(1),
(2) Date: Apr. 18, 2024

(87) PCT Pub. No.: WO2023/071906

PCT Pub. Date: May 4, 2023

(65) Prior Publication Data

US 2024/0407872 A1 Dec. 12, 2024

(30) Foreign Application Priority Data

Oct. 29, 2021 (CN) ........................ 202111272398.0

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/71* (2016.02); *B25J 3/00* (2013.01); *B25J 9/1065* (2013.01);
(Continued)

(58) Field of Classification Search
CPC ... B25J 3/00; B25J 9/106; B25J 9/1065; B25J 19/0016; A61B 34/37; A61B 34/70; A61B 34/71; A61B 2090/5025; A61B 2090/506
See application file for complete search history.

(56) References Cited

U.S. PATENT DOCUMENTS 3,276,604 A * 10/1966 Lemer ........................ G21F 7/00 74/491
7,461,423 B2 * 12/2008 Rutherford ........ F16M 11/2092 5/652
(Continued)

FOREIGN PATENT DOCUMENTS

CN 103919577 A 7/2014
CN 105234959 A * 1/2016 .......... B25J 19/0016
(Continued)

OTHER PUBLICATIONS

Machine translation of CN 207745190 U obtained on Jan. 28, 2026.*
(Continued)

*Primary Examiner* — Adam D Rogers

(57) ABSTRACT

A mechanical arm, a master operating platform, and a surgical robot. The mechanical arm comprises a base link; a parallelogram mechanism rotatably connected to the base link, an axis of rotation of the parallelogram mechanism about the base link coinciding with a first rotational axis between a first linkage and a second linkage in the parallelogram mechanism; and a gravity compensation mechanism, comprising a rotating mechanism and an elastic mechanism, the rotating mechanism being coupled to at least one of the first linkage and the second linkage, as well as the base link, and the elastic mechanism being coupled to the base link and the rotating mechanism, so as to generate a compensation torque to balance gravity moment of the
(Continued)

parallelogram mechanism in at least one degree of freedom corresponding to the parallelogram mechanism.

20 Claims, 9 Drawing Sheets

(51) Int. Cl.

| | |
|---|---|
| ***A61B 90/50*** | (2016.01) |
| ***B25J 3/00*** | (2006.01) |
| ***B25J 9/10*** | (2006.01) |
| ***B25J 19/00*** | (2006.01) |

(52) U.S. Cl.
CPC ... *B25J 19/0016* (2013.01); *A61B 2090/5025* (2016.02); *A61B 2090/506* (2016.02)

(56) References Cited

U.S. PATENT DOCUMENTS

| | | | | |
|---|---|---|---|---|
| 9,375,837 | B2 * | 6/2016 | Nakamura | F21V 21/26 |
| 10,040,207 | B1 * | 8/2018 | Cheng | B25J 19/0012 |
| 10,449,669 | B2 * | 10/2019 | Meuleman | B25J 9/106 |
| 11,986,263 | B2 * | 5/2024 | Wang | A61B 17/00234 |
| 12,161,514 | B2 * | 12/2024 | Chablat | B25J 9/1065 |
| 2018/0193107 | A1 * | 7/2018 | Suh | A61B 90/50 |
| 2021/0393350 | A1 * | 12/2021 | Hongo | A61B 34/70 |
| 2024/0042628 | A1 * | 2/2024 | Biafore | B23K 26/702 |

FOREIGN PATENT DOCUMENTS

| | | | | | |
|---|---|---|---|---|---|
| CN | 105287003 | A | | 2/2016 | |
| CN | 207745190 | U | | 8/2018 | |
| CN | 110236677 | A | | 9/2019 | |
| CN | 112754667 | A | * | 5/2021 | A61B 34/71 |
| CN | 113116404 | A | | 7/2021 | |
| CN | 113543943 | A | | 10/2021 | |
| CN | 115645061 | A | | 1/2023 | |
| DE | 4014003 | A1 | | 10/1991 | |
| TW | I624341 | B | | 5/2018 | |
| WO | 2014108545 | A1 | | 7/2014 | |
| WO | 2015060626 | A1 | | 4/2015 | |
| WO | WO-2019174543 | A1 | * | 9/2019 | A61B 34/37 |
| WO | 2020092516 | A1 | | 5/2020 | |

OTHER PUBLICATIONS

Machine translation of TW I624341 B obtained on Jan. 28, 2026.*

Ruprecht Altenburger et al., Design of a passive, iso-elastic upper limb exoskeleton for gravity compensation, ROBOMECH Journal, Apr. 29, 2016, vol. 3, No. 1.

Wu, Shujiang et al., The design experiment and simulation of parallelogram micro-low gravity balance device with adjustable spring, Proc. of SPIE, Oct. 14, 2021, pp. 1193019-1-1193019-6, vol. 11930, US.

Chen, Yanyan et al., Gravity balance mechanism for a spatial robotic manipulator, Journal of Mechanical Science and Technology, Feb. 10, 2016, pp. 865-869, vol. 30, No. 2, Springer, DE.

International Search Report of PCT Patent Application No. PCT/CN2022/126409 issued on Dec. 22, 2022.

* cited by examiner

MECHANICAL ARM, MASTER OPERATING PLATFORM, AND SURGICAL ROBOT

CROSS-REFERENCE TO RELATED APPLICATION

This application is the U.S. national phase of International Application No. PCT/CN2022/126409 with an international filing date of Oct. 20, 2022, designating the U.S., now pending, and claims the priority of Chinese Patent Application No. 202111272398.0, filed on Oct. 29, 2021, and titled "mechanical arm, master operating platform, and surgical robot", the entirety of which is incorporated by reference herein.

TECHNICAL FIELD

The subject matter herein generally relates to robots, in particular to a mechanical arm and a master operating platform.

BACKGROUND

In the technical fields of industrial robots, medical robots etc., mechanical arms with a specific number of degrees of freedom are more and more widely used in robots.

Taking a laparoscopic surgical robot as an example, the laparoscopic surgical robot includes a master operating platform and a slave operating equipment controlled by the master operating platform. The master operating platform includes a master hand, which includes a mechanical arm with multiple degrees of freedom. Surgeons can generate control commands by manipulating the mechanical arm, thereby controlling the slave operating equipment.

In some existing products, some structures in the mechanical arm of the master hand may easily form a cantilever structure. Consequently, this can lead to issues where the feel of the operation is affected by the gravity of the cantilever structure.

SUMMARY

Based on the aforementioned technical problems, it is necessary to provide a mechanical arm, a master operating platform, and a surgical robot, which can achieve better gravity balance in the gravity-compensated degree of freedom without increasing the inertia of the mechanical arm, thereby providing excellent operation experience.

Aiming at the aforementioned technical problems, the present disclosure provides a mechanical arm. The mechanical arm includes a base link, a parallelogram mechanism, and a gravity compensation mechanism. The parallelogram mechanism comprises a first linkage, a second linkage, a third linkage, and a fourth linkage sequentially connected by rotation, wherein the parallelogram mechanism is rotatably connected to the base link about an axis coinciding with a first rotation axis between the first linkage and the second linkage, and the parallelogram mechanism has a degree of freedom coming from an overall rotation of the parallelogram mechanism relative to the base link and a degree of freedom coming from relative rotation between two adjacent linkages of the parallelogram mechanism. The gravity compensation mechanism comprises a rotating mechanism and an elastic mechanism, wherein the rotating mechanism is coupled to the base link and at least one of the first linkage and the second linkage, and the elastic mechanism is coupled to the base link and the rotating mechanism, so as to generate a compensation moment balanced with a gravity moment of the parallelogram mechanism in at least one degree of freedom associated with the parallelogram mechanism.

In an embodiment, the rotating mechanism comprises a first rotating mechanism, the elastic mechanism comprises a first elastic mechanism, the first rotating mechanism is coupled to the base link and one of the first linkage and the second linkage, and the first elastic mechanism is coupled to the base link and the first rotating mechanism, so as to generate the compensation moment balanced with the gravity moment of the parallelogram mechanism in one degree of freedom associated with the parallelogram mechanism; and/or the rotating mechanism comprises a second rotating mechanism, the elastic mechanism comprises a second elastic mechanism, the second rotating mechanism is coupled to the base link and the other of the first linkage and the second linkage, and the second elastic mechanism is coupled to the base link and the second rotating mechanism, so as to generate the compensation moment balanced with the gravity moment of the parallelogram mechanism in another degree of freedom associated with the parallelogram mechanism.

In an embodiment, the parallelogram mechanism comprises a first degree of freedom, the first degree of freedom comprises the degree of freedom coming from the overall rotation of the parallelogram mechanism about the first rotation axis, the first rotating mechanism is coupled to the base link and the first linkage, and the first elastic mechanism generates the compensation moment balanced with the gravity moment of the parallelogram mechanism in the first degree of freedom In an embodiment, the first rotating mechanism comprises a first rotating component, a second rotating component, a third rotating component and a fourth rotating component, the first rotating component is fixedly connected to the base link, the second rotating component is coaxially provided with the first rotating component and the second rotating component is rotatable with respect to the first rotating component, each of the third rotating component and the fourth rotating component is rotatably connected to the first linkage, a rotation axis of the third rotating component coincides with the first rotation axis, a rotation axis of the second rotating component and a rotation axis of the fourth rotating component are parallel to the first rotation axis; the first elastic mechanism comprises a first clastic element and a first cable, a first end of the first elastic element is connected to the base link, a first end of the first cable is fixedly connected to the first rotating component, a second end of the first cable is sequentially wound around the second rotating component, guided by the third rotating component, wound around the fourth rotating component and connected to a second end of the first elastic element; or the first end of the first elastic element is connected to the base link, the first end of the first cable is fixedly connected to the first rotating component, the second end of the first cable is sequentially wound around the fourth rotating component, guided by the third rotating component, wound around the second rotating component and connected to the second end of the first elastic element.

In an embodiment, an elastic coefficient of the first elastic element, a distance between the rotation axis of the third rotating component and the rotation axis of the second rotating component, and a distance between the rotation axis of the fourth rotating component and the first rotation axis comprise at least one first parameter to be determined, the first parameter to be determined each is determined based on a first condition and a second condition, the first condition comprises gravity of the first linkage, gravity of the third linkage, gravity of the fourth linkage, a distance between a center of gravity of the first linkage and the first rotation axis, a distance from a center of gravity of the third linkage to a second rotation axis between the second linkage and the third linkage, and a distance from a fourth rotation axis between the fourth linkage and the first linkage to the first rotation axis, the second condition comprises parameters other than the first parameter to be determined among the elastic coefficient of the first elastic element, the distance between the rotation axis of the third rotating component and the rotation axis of the second rotating component, and the distance between the rotation axis of the fourth rotating component and the first rotation axis.

In an embodiment, configuration of the first elastic element and the first rotating mechanism satisfies a formula as follows:

$$k1 \times a1 \times b1 < G1 \times L1 + G3 \times L3 + G4 \times L4$$

In the formula, k1 represents the elastic coefficient of the first elastic element, a1 represents the distance between the rotation axis of the fourth rotating component and the rotation axis of the third rotating component, b1 represents the distance between the rotation axis of the third rotating component and the rotation axis of the second rotating component, G1 represents the gravity of the first linkage, G3 represents the gravity of the third linkage, G4 represents the gravity of the fourth linkage, L1 represents the distance between the center of gravity of the first linkage and the first rotation axis, L3 represents the distance from the center of gravity of the third linkage to the second rotation axis between the second linkage and the third linkage, and L4 represents the distance from the fourth rotation axis between the fourth linkage and the first linkage to the first rotation axis.

In an embodiment, the first elastic element comprises a variable-stiffness spring to achieve the clastic coefficient, the distance between the rotation axis of the fourth rotating component and the first rotation axis, and/or the distance between the rotation axis of the third rotating component and the rotation axis of the second rotating component being adjustable.

In an embodiment, the gravity compensation mechanism comprises a first guiding component and a first mounting component, the first guiding component is provided on the first linkage, the first mounting component is movably provided in the first guiding component, and the fourth rotating component is rotatably mounted on the first mounting component; and/or the gravity compensation mechanism comprises a second guiding component and a second mounting component, the second guiding component is provided on the base link, the first rotating component is fixedly mounted on the second mounting component, and the second rotating component is rotatably mounted on the second mounting component.

In an embodiment, the first guiding component and/or the second guiding component comprises a slide groove or a slide rail; the first rotating component, the second guiding component, the third rotating component and the fourth rotating component comprise pulleys.

In an embodiment, the gravity compensation mechanism further comprises a first driving mechanism coupled to the first guiding component or the first mounting component to drive the first mounting component to move in the first guiding component, thereby driving the fourth rotating component to move relative to the first linkage; and/or the gravity compensation mechanism further comprises a second driving mechanism coupled to the second guiding component or the second mounting component to drive the second mounting component to move in the second guiding component, thereby driving the first rotating component and the second rotating component to move relative to the base link.

In an embodiment, the parallelogram mechanism comprises a second degree of freedom, the second degree of freedom comprises the degree of freedom coming from the relative rotation between the two adjacent linkages of the parallelogram mechanism, the second rotating mechanism is coupled to the base link and the second linkage, and the second clastic mechanism generates the compensation moment balanced with the gravity moment of the parallelogram mechanism in the second degree of freedom.

In an embodiment, the second rotating mechanism comprises a fifth rotating component, a seventh rotating component, and an eighth rotating component, the fifth rotating component is fixedly connected to the base link, each of the seventh rotating component and the eighth rotating component is rotatably connected to the second linkage, a rotation axis of the seventh rotating component coincides with the first rotation axis, a rotation axis of the fifth rotating component and a rotation axis of the eighth rotating component are parallel to the first rotation axis; the second elastic mechanism comprises a second elastic element and a second cable, a first end of the second elastic element is connected to the base link, a first end of the second cable is fixedly connected to the fifth rotating component, a second end of the second cable is sequentially guided by the seventh rotating component, wound around the eighth rotating component and connected to a second end of the second elastic element; or the first end of the second elastic element is connected to the base link, the first end of the second cable is fixedly connected to the fifth rotating component, the second end of the second cable is sequentially wound around the eighth rotating component, guided by the seventh rotating component and connected to the second end of the second elastic element.

In an embodiment, an elastic coefficient of the second elastic element, a distance between the rotation axis of the seventh rotating component and the rotation axis of the fifth rotating component, and a distance between the rotation axis of the eighth rotating component and the rotation axis of the seventh rotating component comprise at least one second parameter to be determined, the second parameter to be determined each is determined based on a third condition and a fourth condition, the third condition comprises gravity of the second linkage, gravity of the third linkage, gravity of the fourth linkage, a distance between a center of gravity of the second linkage and the first rotation axis, a distance from a second rotation axis between the second linkage and the third linkage to the first rotation axis, and a distance from a center of gravity of the fourth linkage to a fourth rotation axis between the fourth linkage and the second linkage, the fourth condition comprises parameters other than the second parameter to be determined among the elastic coefficient of the second elastic element, the distance between the rotation axis of the seventh rotating component and the rotation axis of the fifth rotating component, and the distance between the rotation axis of the eighth rotating component and the rotation axis of the seventh rotating component.

In an embodiment, configuration of the second elastic element and the second rotating mechanism satisfies a formula as follows:

$$k2 \times a2 \times b2 \geq G2 \times L2' + G3 \times L3' + G4 \times L4',$$

In the formula, k2 represents the elastic coefficient of the second elastic element, a2 represents the distance between the rotation axis of the eighth rotating component and the rotation axis of the seventh rotating component, b2 represents the distance between the rotation axis of the seventh rotating component and the rotation axis of the fifth rotating component, G2 represents the gravity of the second linkage, G3 represents the gravity of the third linkage, G4 represents the gravity of the fourth linkage, L2' represents the distance between the center of gravity of the second linkage and the first rotation axis, L3' represents the distance from the second rotation axis between the second linkage and the third linkage to the first rotation axis, and L4' represents the distance from the center of gravity of the fourth linkage to the fourth rotation axis between the fourth linkage and the second linkage.

In an embodiment, the second elastic element comprises a variable-stiffness spring to achieve the elastic coefficient, the distance between the rotation axis of the eighth rotating component and the first rotation axis, and/or the distance between the rotation axis of the seventh rotating component and the rotation axis of the fifth rotating component being adjustable.

In an embodiment, the gravity compensation mechanism comprises a third guiding component and a third mounting component, the third guiding component is provided on the second linkage, the third mounting component is movably provided in the third guiding component, and the eighth rotating component is rotatably mounted on the third mounting component; and/or the gravity compensation mechanism comprises a fourth guiding component and a fourth mounting component, the fourth guiding component is provided on the base link, the fourth mounting component is movably provided on the fourth guiding component, and the fifth rotating component is fixedly mounted on the fourth mounting component.

In an embodiment, the third guiding component and/or the fourth guiding component comprises a slide groove or a slide rail; the fifth rotating component, the seventh rotating component and the eighth rotating component comprise pulleys.

In an embodiment, the gravity compensation mechanism further comprises a third driving mechanism coupled to the third guiding component or the third mounting component to drive the third mounting component to move in the third guiding component, thereby driving the eighth rotating component to move relative to the second linkage; and/or the gravity compensation mechanism further comprises a fourth driving mechanism coupled to the fourth guiding component or the fourth mounting component to drive the fourth mounting component to move in the fourth guiding component, thereby driving the fifth rotating component to move relative to the base link.

In an embodiment, the gravity compensation mechanism further comprises a first motor coupled to the first linkage to actively compensate for the gravity moment in the degree of freedom coming from the overall rotation of the parallelogram mechanism about the first rotation axis; and/or the gravity compensation mechanism further comprises a second motor coupled to the second linkage to actively compensate for the gravity moment in the degree of freedom coming from the relative rotation between the adjacent linkages of the parallelogram mechanism.

In an embodiment, the diameters of the first rotating component, the second rotating component, the third rotating component and the fourth rotating component are the same; and/or the diameters of the fifth rotating component and the seventh rotating component and the eighth rotating component are the same.

In an embodiment, an angle range of the rotation between the two adjacent linkages in the parallelogram mechanism is $\theta \in (0°, 180°)$.

In an embodiment, the parallelogram mechanism comprises a load connected to a distal end of the parallelogram mechanism, and the gravity compensation mechanism is further configured to generate a compensation moment balanced with a gravity moment of the parallelogram mechanism comprising the load.

Aiming at the aforementioned technical problems, the present disclosure provides a master operating platform. The master operating platform includes an operating portion configured to generate a control command which comprises a pose instruction, wherein the operation portion comprises the mechanical arm according to any one of the aforementioned embodiments.

Aiming at the aforementioned technical problems, the present disclosure provides a surgical robot. The surgical robot includes a slave operating equipment and the master operating platform according to any one of the aforementioned embodiments, wherein the slave operating equipment performs a corresponding operation based on the control command from the master operating platform.

Aiming at the aforementioned technical problems, the present disclosure provides an installation method for a mechanical arm. The installation method includes: providing a base link; providing a parallelogram mechanism comprising a first linkage, a second linkage, a third linkage, and a fourth linkage sequentially connected by rotation, rotatably connecting the parallelogram mechanism to the base link about an axis coinciding with a first rotation axis between the first linkage and the second linkage; providing a rotating mechanism and an clastic mechanism, coupling the rotating mechanism to the base link and at least one of the first linkage and the second linkage, and coupling the elastic mechanism to the base link and the rotating mechanism to generate a compensation moment balanced with a gravity moment of the parallelogram mechanism in at least one degree of freedom associated with the parallelogram mechanism.

In an embodiment, the rotating mechanism comprises a first rotating mechanism, the elastic mechanism comprises a first elastic mechanism, the installation method includes: coupling the first rotating mechanism to the base link and one of the first linkage and the second linkage, and coupling the first elastic mechanism to the base link and the first rotating mechanism to generate the compensation moment balanced with the gravity moment of the parallelogram mechanism in one degree of freedom associated with the parallelogram mechanism.

In an embodiment, the rotating mechanism comprises a second rotating mechanism, the clastic mechanism comprises a second clastic mechanism, the installation method includes: coupling the second rotating mechanism to the base link and the other of the first linkage and the second linkage, and coupling the second elastic mechanism to the base link and the second rotating mechanism to generate the compensation moment balanced with the gravity moment of the parallelogram mechanism in another degree of freedom associated with the parallelogram mechanism.

The mechanical arm, the master operating platform, and the surgical robot provided by the present disclosure offer the following advantages:

By coupling the rotating mechanism in the gravity compensation mechanism to the base link and at least one of the first linkage and the second linkage in the parallelogram mechanism, and coupling the elastic mechanism to the base link and the rotating mechanism, the compensation moment can be generated in at least one degree of freedom corresponding to the parallelogram mechanism to balance the gravity moment of the parallelogram mechanism, thereby achieving excellent gravity balancing in the gravity-compensated degree of freedom without increasing the inertia of the mechanical arm and providing an exceptional operation experience.

DETAILED DESCRIPTION

The present disclosure will be described clearly and thoroughly herein by accompanying with appended figures of some embodiments. Apparently, the embodiments are only component of the present disclosure, and are not the whole disclosure. For the person of ordinary skill in the art, other embodiments may be obtained based on the provided embodiments without any creative work, and the other embodiments are also covered by the present disclosure. The preferred embodiments of the present disclosure are illustrated in the accompanying drawings. However, it should be understood that the present disclosure can be implemented in many different forms and is not limited to the embodiments described herein. On the contrary, these embodiments are provided to enable a more thorough and comprehensive understanding of the present disclosure.

It should be noted that when an element is referred to as being "disposed on" or "provided on" another element, it can be directly on the other element or intervening elements may also be present. When an element is considered to be "connected" to another element, it can be directly connected to the other element or intervening elements may also be present. Similarly, when an element is considered to be "coupled" to another element, it can be directly coupled to the other element or intervening elements may also be present. The terms "distal" and "proximal" are used herein as orientation terms and are commonly used in the field of interventional medical devices, where "distal" refers to the end that is away from the operator during a procedure and "proximal" refers to the end that is close to the operator during a procedure. The term "plurality" as used herein includes two or more.

Unless otherwise defined, all technical and scientific terms used herein have the same meaning as commonly understood by one of ordinary skill in the art to which this application belongs. The terms used in the specification of the present disclosure are for the purpose of describing specific embodiments only and are not intended to limit the application. The term "and/or" as used herein includes any and all combinations of one or more of the associated listed items.

Figure 1:
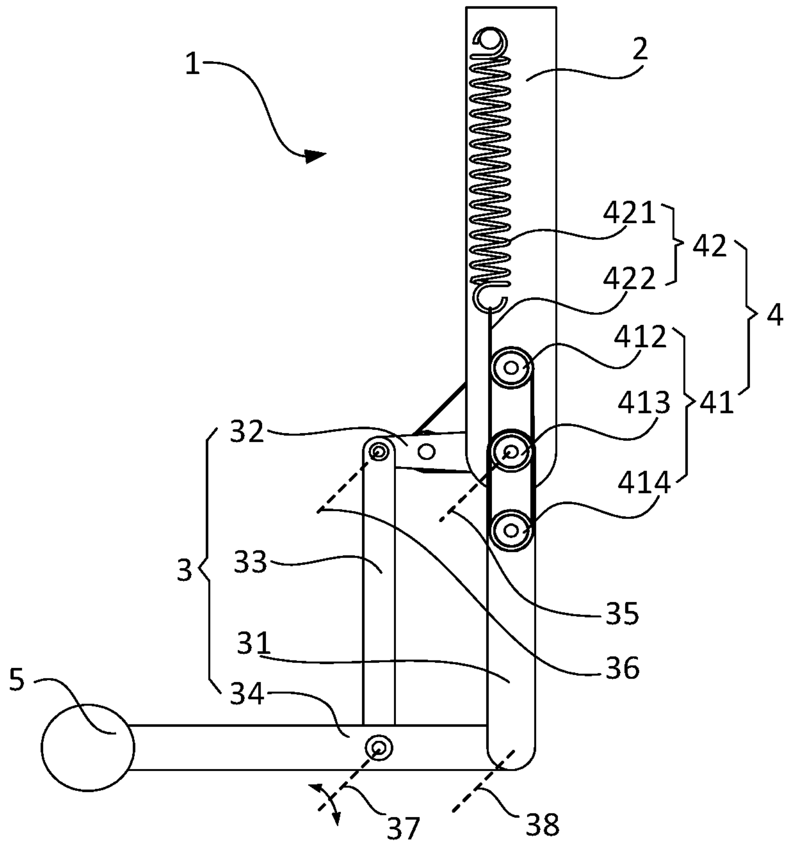
FIG. 1 is a schematic view of a mechanical arm according to an embodiment of the present disclosure.

Referring to FIG. 1, the mechanical arm 1 according to the present disclosure comprises a base link 2, a parallelogram mechanism 3, and a gravity compensation mechanism 4. The parallelogram mechanism 3 is coupled to the base link 2, and the gravity compensation mechanism 4 is coupled between the base link 2 and the parallelogram mechanism 3. The gravity compensation mechanism 4 generates a compensation moment balanced with a gravity moment of the parallelogram mechanism 3. In some embodiments, the parallelogram mechanism 3 may further include a load 5 connected to a distal end of the parallelogram mechanism 3. Typically, the load 5 may include any mechanism connected to the distal end of the parallelogram mechanism 3, such as one or more additional linkages.

In some embodiments, the parallelogram mechanism 3 is rotatably connected to the base link 2. One degree of freedom can be provided for the mechanical arm 1 through the rotational connection between the parallelogram mechanism 3 and the base link 2. The parallelogram mechanism 3 comprises a first linkage 31, a second linkage 32, a third linkage 33, and a fourth linkage 34 which are sequentially connected by rotation. The relative motion between adjacent linkages of the parallelogram mechanism 3 can provide another degree of freedom for the mechanical arm 1. Furthermore, the mechanical arm 1 has at least two degrees of freedom based on these two degrees of freedom associated with the parallelogram mechanism 3. Typically, the gravity compensation mechanism 4 comprises a rotating mechanism and an elastic mechanism. The rotating mechanism is distributed on the base link 2 and at least one of the first linkage 31 and the second linkage 32, and the clastic mechanism is coupled to the base link 2 and the rotating mechanism, so as to generate a compensation moment balanced with the gravity moment of the parallelogram mechanism 3 in at least one degree of freedom associated with the parallelogram mechanism 3.

In the parallelogram mechanism 3, there is a first rotation axis 35 between the first linkage 31 and the second linkage 32, a second rotation axis 36 exists between the second linkage 32 and the third linkage 33, a third rotation axis 37 exists between the third linkage 33 and the fourth linkage 34, and a fourth rotation axis 38 between the fourth linkage 34 and the first linkage 31. Two adjacent linkages can rotate about the rotation axis between them.

The axis of the overall rotation of the parallelogram mechanism 3 relative to the base link 2 coincides with the first rotation axis 35, that is, the parallelogram mechanism 3 as a whole can rotate about the first rotation axis 35.

In some embodiments, the base link 2 may be fixedly provided. For instance, the base link 2 may be fixed to a base of a certain device, or the base link 2 may be fixed to a wall, ceiling, etc.

In some embodiments, the base link 2 can be movably provided. Typically, the base link 2 can be movable through being coupled to the distal end of one or more proximal linkages. For instance, the base link 2 can be configured to translate in the direction of gravity, translate in the direction perpendicular to the direction of gravity, or rotate about its axis parallel to the direction of gravity.

In some embodiments, the gravity compensation mechanism 4 comprises a first rotating mechanism 41 and a first elastic mechanism 42. The first rotating mechanism 41 includes multiple rotating components distributed on the base link 2 and the first linkage 31, or theses rotating components can be distributed on the base link 2 and the second linkage 32. For case of understanding, the first rotating mechanism 41 can comprise first part of rotating components and second part of rotating components. Exemplarily, the first part of rotating components can be disposed on the base link 2, while the second part of rotating components can be disposed on the first linkage 31; alternatively, the first part of rotating components can be disposed on the base link 2, while the second part of rotating components can be disposed on the second linkage 32. Typically, the first elastic mechanism 42 is coupled between the base link 2 and the first rotating mechanism 41 to generate a compensation moment balanced with the gravity moment of the parallelogram mechanism 3 in one degree of freedom associated with the parallelogram mechanism 3, which allows the user to easily perform a dragging operation on the mechanical arm 1 in said degree of freedom.

Figure 2:
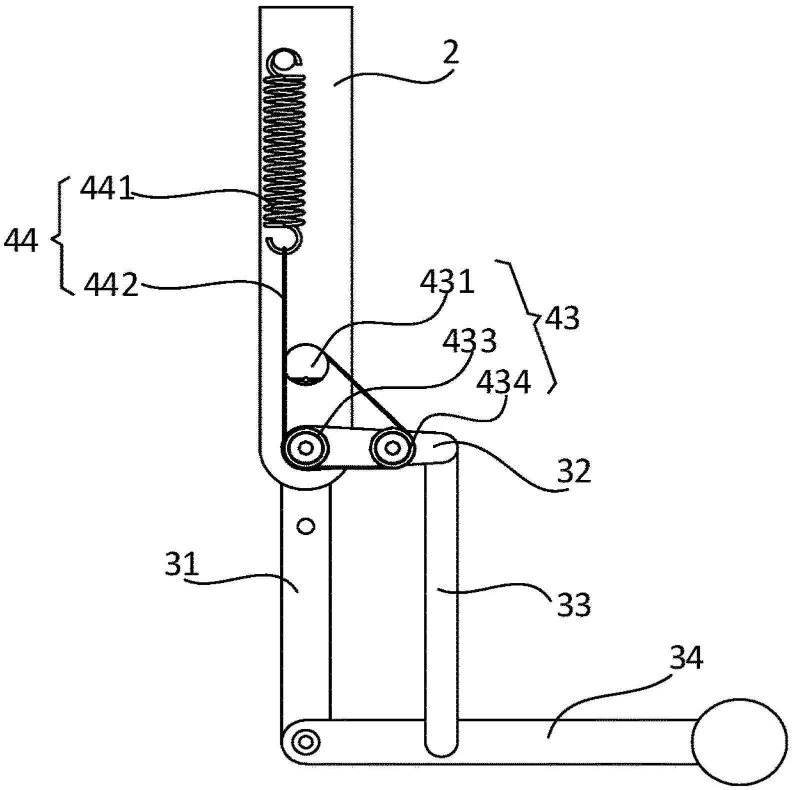
FIG. 2 is a schematic view of a mechanical arm according to another embodiment of the present disclosure.

In some embodiments, as shown in FIG. 2, the gravity compensation mechanism 4 includes a second rotating mechanism 43 and a second elastic mechanism 44. The second rotating mechanism 43 comprises multiple rotating components distributed on the base link 2 and the second linkage 32, or theses rotating components can be distributed on the base link 2 and the first linkage 31. For ease of understanding, the second rotating mechanism 43 can comprise first part of rotating components and second part of rotating components. Exemplarily, the first part of rotating components can be disposed on the base link 2, while the second part of rotating components can be disposed on the second linkage 32; alternatively, the first part of rotating components can be disposed on the base link 2, while the second part of rotating components can be disposed on the first linkage 31. Typically, the second elastic mechanism 44 is coupled between the base link 2 and the second rotating mechanism 43 to generate a compensation moment balanced with the gravity moment of the parallelogram mechanism 3 in another degree of freedom associated with the parallelogram mechanism 3, which allows the user to easily perform a dragging operation on the mechanical arm 1 in said degree of freedom.

Figure 3:
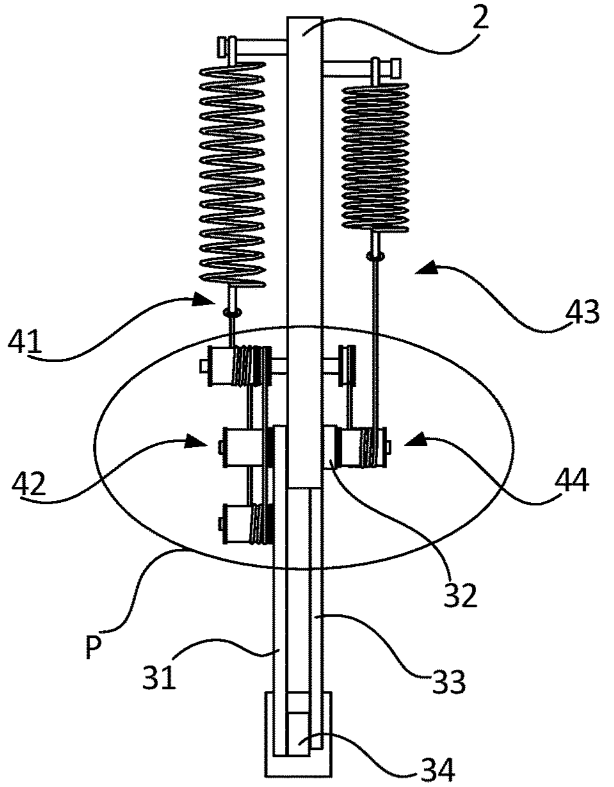
FIG. 3 is a schematic view of a mechanical arm according to yet another embodiment of the present disclosure.

In some embodiments, as shown in FIG. 3, the gravity compensation mechanism 4 can include the first rotating mechanism 41, the first elastic mechanism 42, the second rotating mechanism 43, and the second elastic mechanism 44. For instance, when the first part of rotating components of the first rotating mechanism 41 is disposed on the base link 2 and the second part of rotating components of the first rotating mechanism 41 is disposed on the first linkage 31, the first part of rotating components of the second rotating mechanism 43 is typically disposed on the base link 2 and the second part of rotating components of the second rotating mechanism 43 is typically disposed on the second linkage 32. Alternatively, when the first part of rotating components of the first rotating mechanism 41 is disposed on the base link 2 and the second part of rotating components of the first rotating mechanism 41 is disposed on the second linkage 32, the first part of rotating components of the second rotating mechanism 43 is typically disposed on the base link 2 and the second part of rotating components of the second rotating mechanism 43 is typically disposed on the first linkage 31. Thus, the gravity compensation mechanism 4 can provide compensation moments for the corresponding gravity moments in two degrees of freedom of the parallelogram associated with mechanism 3 respectively, which allows the user to easily perform a dragging operation on the mechanical arm 1 in said two degrees of freedom.

In the aforementioned embodiments, the rotating components of the first rotating mechanism 41 and/or the second rotating mechanism 43 can include pulleys and/or rotating shafts. For instance, each rotating component can be configured as a pulley.

In some embodiments, referring to FIG. 3, the degrees of freedom associated with the parallelogram mechanism 3 include a first degree of freedom and a second degree of freedom. Exemplarily, the first degree of freedom includes the degree of freedom coming from the overall rotation of the parallelogram mechanism 3 about the first rotation axis 35, while the second degree of freedom the degree of freedom coming from the relative rotation between the two adjacent linkages of the parallelogram mechanism 3 (e.g., the degree of freedom coming from rotation between the second linkage 32 and the first linkage 31). When the gravity compensation mechanism 4 includes the first rotating mechanism 41, the first clastic mechanism 42, the second rotating mechanism 43, and the second clastic mechanism 44 as described above, compensation moments can be provided for the corresponding gravity moments in the first and second degrees of freedom respectively.

Figure 4:
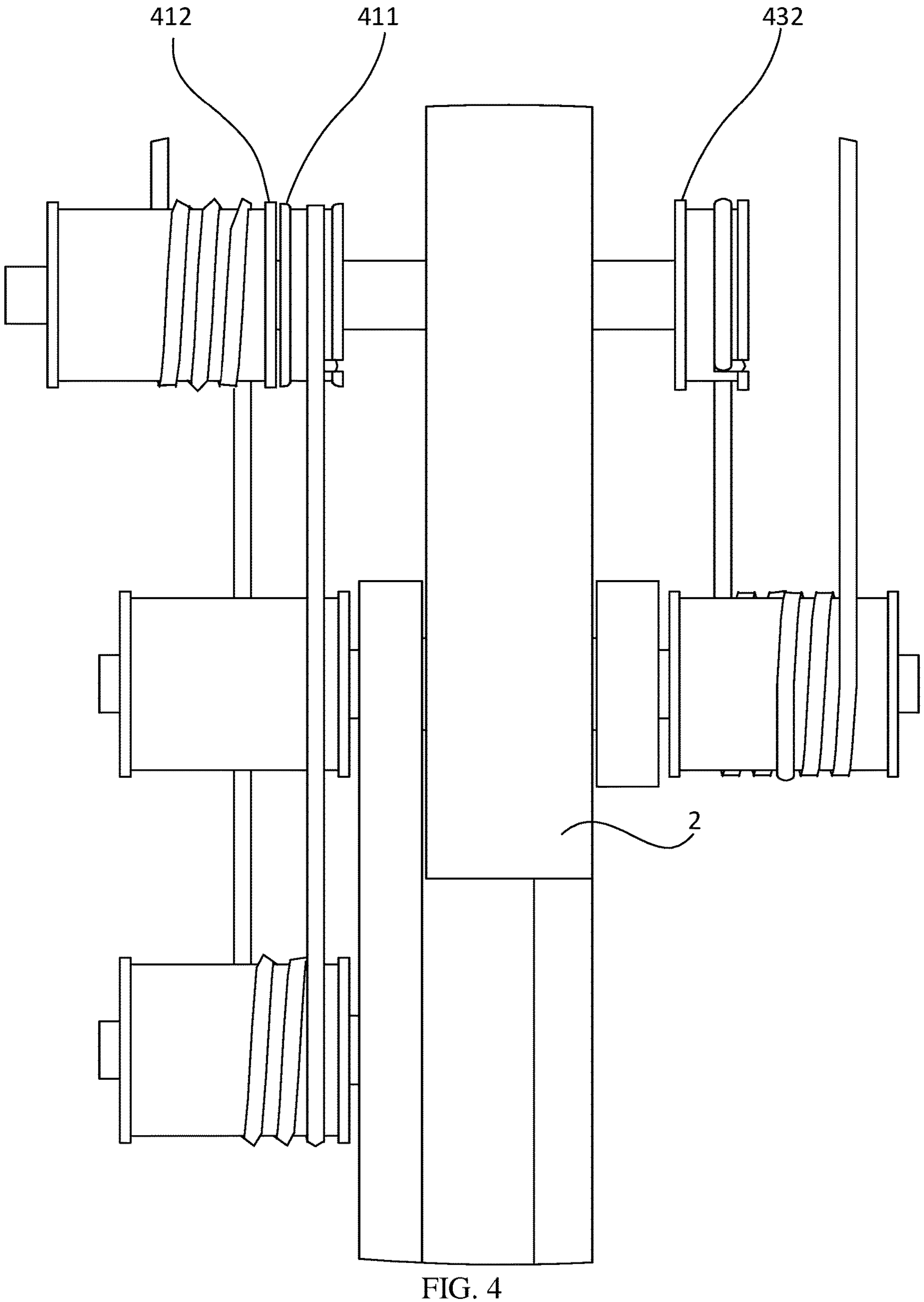
FIG. 4 is an enlarged view of the structure at P in the mechanical arm of FIG. 3.

In some embodiments, referring to FIG. 1 and FIG. 4, the first rotating mechanism 41 comprises a first rotating component 411, a second rotating component 412, a third rotating component 413, and a fourth rotating component 414. The first rotating component 411 is fixedly connected to the base link 2, while the second rotating component 412 is coaxially provided with the first rotating component 411 and the second rotating component 412 is rotatable with respect to the first rotating component 411. Each of the third rotating component 413 and the fourth rotating component 414 is rotatably connected to the first linkage 31. The rotation axis of the third rotating component 413 coincides with the first rotation axis 35, and the rotation of the third rotating component 413 is independent of the overall rotation of the parallelogram mechanism 3 about the first rotation axis 35.

The rotation axis of the second rotating component 412 and the rotation axis of the fourth rotating component 414 are parallel to the first rotation axis 35. Exemplarily, the second rotating component 412, the third rotating component 413, and the fourth rotating component 414 can be disposed on the same side wall of the base link 2 and the parallelogram mechanism 3 to facilitate the arrangement of the first elastic mechanism 42.

Figure 5:
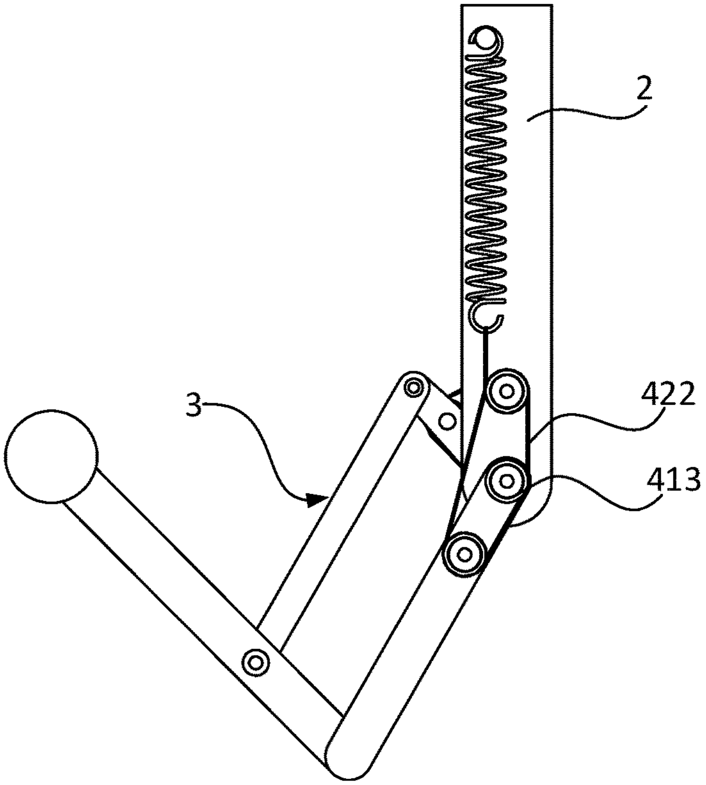
FIG. 5 is a schematic view of the mechanical arm of FIG. 1 in a movement state.
Figure 6:
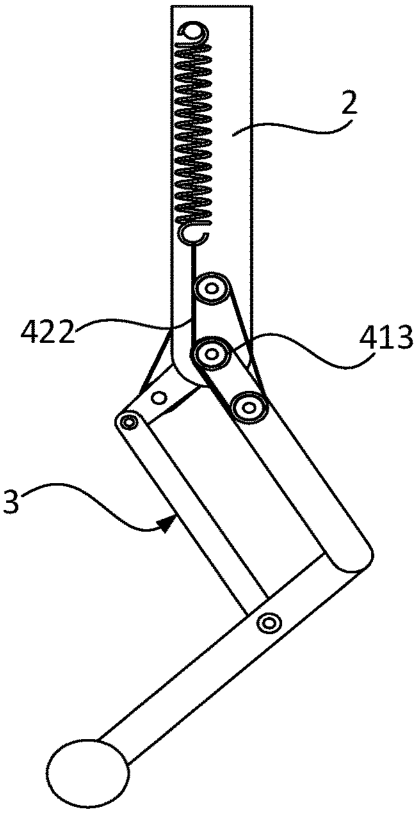
FIG. 6 is a schematic view of the mechanical arm of FIG. 1 in another movement state.

Furthermore, the first clastic mechanism 42 includes a first clastic element 421 and a first cable 422. In some embodiments, the first elastic element 421 and the first cable 422 can be arranged as follows. Specifically, the first end of the first elastic element 421 is connected to the base link 2, while the first end of the first cable 422 is fixedly connected to the first rotating component 411. The second end of the first cable 422 is sequentially wound around the second rotating component 412, guided by the third rotating component 413, wound around the fourth rotating component 414, and connects to the second end of the first clastic element 421. In other embodiments, the first clastic element 421 and the first cable 422 can be arranged as follows. Alternatively, the first end of the first clastic element 421 is connected to the base link 2, while the first end of the first cable 422 is fixedly connected to the first rotating component 411. The second end of the first cable 422 is sequentially wound around the fourth rotating component 414, guided by the third rotating component 413, wound around the second rotating component 412, and connect to the second end of the first elastic element 421. Typically, the first cable 422 being guided by the third rotating component 413 comprises the first cable 422 being provided tangentially to the third rotating component 413 so as not to interfere with the commutation of the parallelogram mechanism 3 in the first degree of freedom. As shown in FIG. 1, when the parallelogram mechanism 3 is in a neutral position, i.e., when the parallelogram mechanism 3 as a whole is not rotated to the left or the right of the base link 2, the first cable 422 is tangential to both the left and right sides of the third rotating portion 413. As shown in FIG. 5, when the parallelogram mechanism 3 is rotated to the left of the base link 2, the first cable 422 is tangential to the right side of the third rotating portion 413. As shown in FIG. 6, when the parallelogram mechanism 3 is rotated to the right of the base link 2, the first cable 422 is tangential to the left side of the third rotating portion 413. The structural design can provide a certain degree of compensation moment for the corresponding gravity moment with the help of the first elastic element 421 in the first degree of freedom.

In some embodiments, the elastic coefficient of the first elastic element 421, the distance between the rotation axis of the third rotating component 413 and the rotation axis of the second rotating component 412 (i.e., the distance between the rotation axis of the second rotating component 412 and the first rotation axis 35), and the distance between the rotation axis of the fourth rotating component 414 and the first rotation axis 35 include at least one first parameter to be determined. The first parameter to be determined each is determined based on a first condition and a second condition. The first condition includes gravity of the first linkage 31, gravity of the third linkage 33, gravity of the fourth linkage 34, the distance between the center of gravity of the first linkage 31 and the first rotation axis 35, the distance from the center of gravity of the third linkage 33 to the second rotation axis between the second linkage 32 and the third linkage 33, and the distance from the fourth rotation axis 38 between the fourth linkage 34 and the first linkage 31 to the first rotation axis 35. The second condition includes parameters other than the first parameter to be determined among the elastic coefficient of the first elastic element 421, the distance between the rotation axis of the third rotating component 413 and the rotation axis of the second rotating component 412, and the distance between the rotation axis of the fourth rotating component 414 and the first rotation axis 35.

In some embodiments, referring to FIG. 2 and FIG. 4, the second rotating mechanism 43 comprises a fifth rotating component 431, a sixth rotating component 432, a seventh rotating component 433, and an eighth rotating component 434. Exemplarily, the fifth rotating component 431 comprises a fifth pulley, the sixth rotating component 432 comprises a sixth pulley, the seventh rotating component 433 comprises a seventh pulley, and the eighth rotating component 434 comprises an eighth pulley. The fifth rotating component 431 is fixedly connected to the base link 2, the sixth rotating component 432 is coaxially provided with the fifth rotating component 431 and the sixth rotating component 432 is rotatable with respect to the fifth rotating component 431. Each of the seventh rotating component 433 and the eighth rotating component 434 is rotatably connected to the second linkage 32. The rotation axis of the seventh rotating component 433 coincides with the first rotation axis 35, and the rotation of the seventh rotating component 433 and the overall rotation of the parallelogram mechanism 3 about the first rotation axis 35 are independent of each other. The rotation axes of the sixth rotating component 432 and the eighth rotating component 434 are parallel to the first rotation axis 35. Typically, the sixth rotating component 432, the seventh rotating component 433, and the eighth rotating component 434 can be arranged on the same side wall of the base link 2 and the parallelogram mechanism 3. When the gravity compensation mechanism 4 includes the first rotating mechanism 41 and the second rotating mechanism 43, the rotating components of the first rotating mechanism 41 and the rotating components of the second rotating mechanism 43 can typically be disposed on different side walls of the parallelogram mechanism 3 to prevent the inaccurate compensation moment caused by mutual interference when laying out elastic elements and cables.

Figure 7:
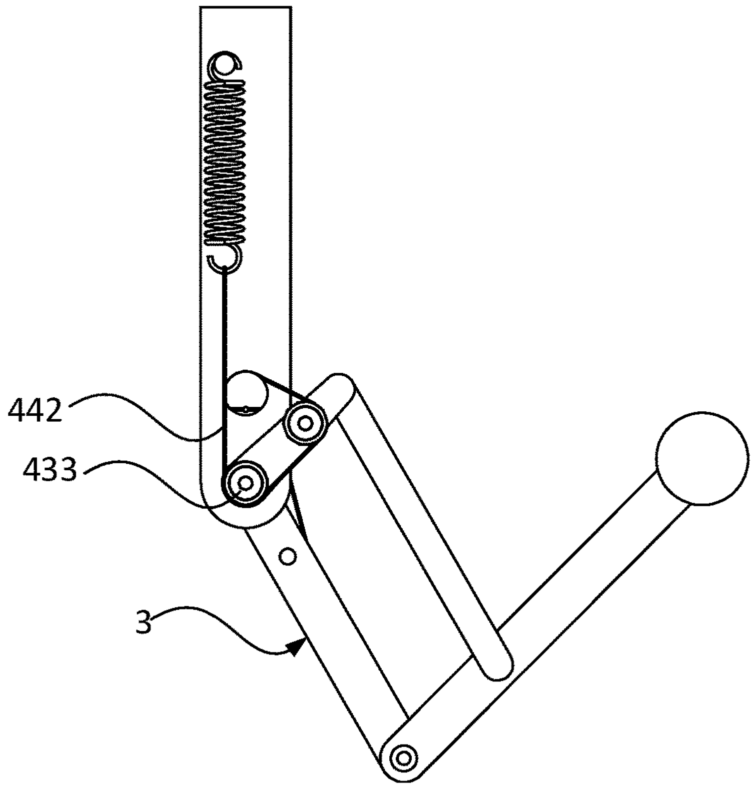
FIG. 7 is a schematic view of the mechanical arm of FIG. 2 in a movement state.
Figure 8:
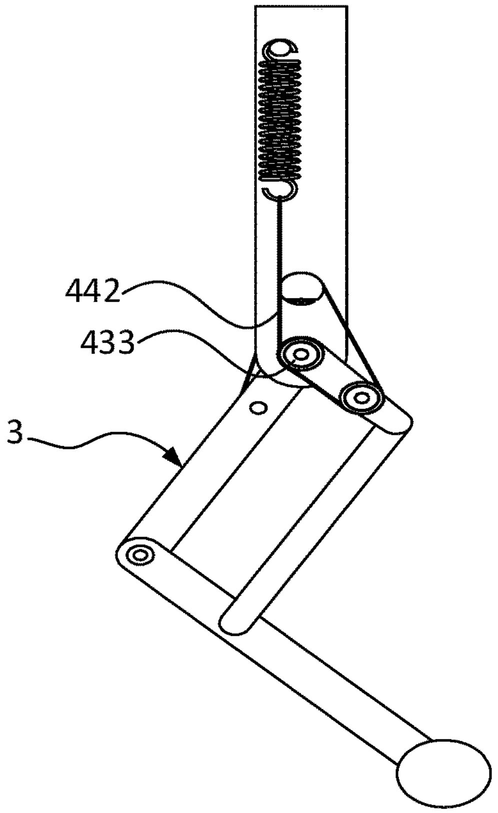
FIG. 8 is a schematic view of the mechanical arm of FIG. 2 in another movement state.

Furthermore, the second elastic mechanism 44 includes a second clastic element 441 and a second cable 442. In some embodiments, the second clastic element 441 and the second cable 442 can be arranged as follows. Specifically, a first end of the second clastic element 441 is connected to the base link 2, and a first end of the second cable 442 is fixedly connected to the fifth rotating component 431. A second end of the second cable 442 is sequentially wound around the sixth rotating component 432, guided by the seventh rotating component 433, wound around the eighth rotating component 434, and connected to a second end of the second clastic element 441. In other embodiments, the second elastic element 441 and the second cable 442 can be arranged as follows. Specifically, the first end of the second clastic element 441 is connected to the base link 2, and the first end of the second cable 442 is fixedly connected to the fifth rotating component 431. The second end of the second cable 442 is sequentially wound around the eighth rotating component 434, guided by the seventh rotating component 433, wound around the sixth rotating component 432, and connected to the second end of the second clastic element 441. Typically, the second cable 442 being guided by the seventh rotating component 433 can include the second cable 442 arranged to be tangent to and wound around the seventh rotating component 433. Referring to FIGS. 2, 7, and 8, regardless of whether the second linkage 32 in the parallelogram mechanism 3 is in a neutral position, rotated upward, or rotated downward with respect to the first linkage 31, the second cable 442 remains tangent to the right side of the seventh rotating component 433. The structural design can provide a certain degree of compensation moment for the corresponding gravity moment with the help of the second elastic element 441 in the second degree of freedom.

In some embodiments, the sixth rotating component 432 according to the present disclosure, which is coaxial with and rotatable relative to the fifth rotating component, can be omitted. That is, it is feasible to retain the fifth rotating component 431 as the rotating component coupled to the base link 2. When only the fifth rotating component 431 is retained, the second clastic element 441 and the second cable 442 can be arranged as follows. Specifically, the first end of the second elastic element 441 is connected to the base link 2, the first end of the second cable 442 is fixedly connected to the fifth rotating component 431, and the second end of the second cable 442 is sequentially wound around the eighth rotating component 434, guided by the seventh rotating component 433, and connected to the second end of the second elastic element 441.

The first cable 422 and the second cable 442 according to the present disclosure include rigid cables comprising cables which are non-stretchable along their axial direction.

In some embodiments, the elastic coefficient of the second elastic element 441, the distance between the rotation axis of the seventh rotating component 433 and the rotation axis of the fifth rotating component 431 (i.e., the distance between the rotation axis of the seventh rotating component 433 and the first rotation axis 35), and the distance between the rotation axis of the eighth rotating component 434 and the rotation axis of the seventh rotating component 433 comprises at least one second parameter to be determined. The second parameter to be determined is determined based on a third condition and a fourth condition. The third condition includes the gravity of the second linkage 32, the gravity of the third linkage 33, the gravity of the fourth linkage 34, the distance between the center of gravity of the second linkage 32 and the first rotation axis 35, the distance from the second rotation axis 36 between the second linkage 32 and the third linkage 33 to the first rotation axis 35, and the distance from the center of gravity of the fourth linkage 34 to the fourth rotation axis 38 between the fourth linkage 34 and the first linkage 31. The fourth condition includes parameters other than the second parameter to be determined among the elastic coefficient of the second elastic element 441, the distance between the rotation axis of the seventh rotating component 433 and the rotation axis of the fifth rotating component 431, and the distance between the rotation axis of the eighth rotating component 434 and the rotation axis of the seventh rotating component 433.

When the third rotating component 413 and the seventh rotating component 433 are provided for gravity compensation in different degrees of freedom of the parallelogram mechanism 3, the rotation of the third rotating component 413 and the rotation of the seventh rotating component 433 are independent of each other.

The term "coinciding" described herein includes both complete coinciding and substantial coinciding between the axes, wherein substantial overlap allows for appropriate offsets between the axes. The term "parallel" described herein includes complete parallelism and substantial parallelism between axes, wherein substantial parallelism allows for appropriate offsets between the axes.

The principle of gravity compensation performed by the gravity compensation mechanism 4 will be described in detail.

Figure 9:
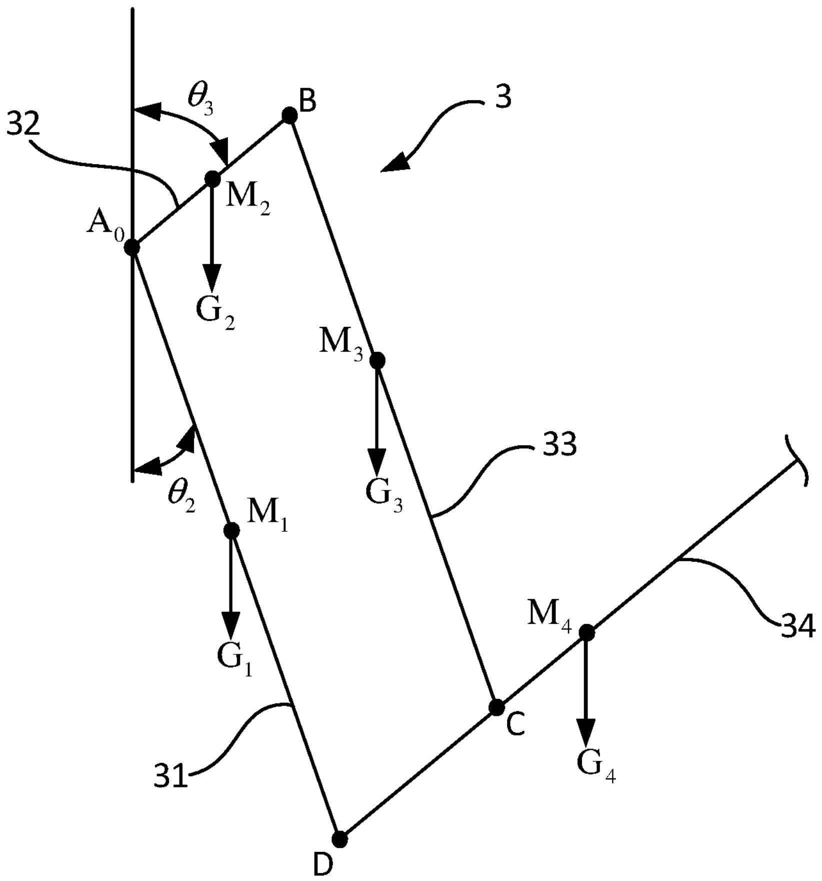
FIG. 9 is a schematic view of the principle of analyzing the gravity of the parallelogram mechanism of the mechanical arm of FIG. 1.

Referring to FIG. 9, in a simplified parallelogram mechanism 3, let the four vertices (i.e., hinge points of the linkages) of the parallelogram mechanism 3 be A0, B, C, and D respectively, and let vertex A0 be the vertex at which the parallelogram mechanism 3 as a whole rotates with respect to the base link 2. Let the linkage between A0 and B be the first linkage 31, the linkage between A0 and D be the second linkage 32, the linkage between C and D be the third linkage 33, and the linkage between B and C be the fourth linkage 34. Let the center of gravity (position) of the first linkage 31 be M1, the center of gravity (position) of the second linkage 32 be M2, the center of gravity (position) of the third linkage 33 be M3, and the center of gravity (position) of the fourth linkage 34 be M4. Furthermore, let the gravity of the first linkage 31 be G1, the gravity of the second linkage 32 be G2, the gravity of the third linkage 33 be G3, and the gravity of the fourth linkage 34 be G4. $\theta_2$ comprises the angle of the overall rotation of the parallelogram mechanism 3 with respect to the base link 2, i.e., $\theta_2$ is associated with the first degree of freedom. $\theta_3$ comprises the angle of rotation between adjacent linkages of the parallelogram mechanism 3, i.e., $\theta_3$ is associated with the second degree of freedom. Since the first degree of freedom and the second degree of freedom are independent of each other, as shown in the FIGS., when adjusting the second degree of freedom alone, the position of the first linkage 31 remains unchanged, while the positions of the second linkage 32, the third linkage 33, and the fourth linkage 34 change accordingly. Further, considering the whole parallelogram mechanism 3 as the object of analysis, a moment equilibrium equation can be established for the force situation at vertex A0. The moment equilibrium equation is given by the following formula (1):

$$\sum M_{A0} = G_1 * M_1A_0 * \sin\theta_2 + G_2 * M_2A_0 * \sin\theta_3 + G_3 * (DM_3 * \sin\theta_2 + DA_0 * \sin\theta_3) + G_4 * (BA_0 * \sin\theta_2 + BM_4 * \sin\theta_3)$$

Simplifying the aforementioned formula (1) yields the following formula (2):

$$\sum M_{A0} = (G_1 * M_1A_0 + G_3 * DM_3 + G_4 * BA_0) * \sin\theta_2 + (G_2 * M_2A_0 + G_3 * DA_0 + G_4 * BM_4) * \sin\theta_3$$

Wherein the distance from the center of gravity $M_1$ to vertex $A_0$ be $M_1A_0$=L1, the distance from vertex D to the center of gravity $M_3$ be $DM_3$=L3, the distance from vertex B to vertex be $BA_0$=L4, the distance from the center of gravity $M_2$ to vertex $A_0$ be $M_2A_0$=L2', the distance from vertex D to vertex $A_0$ be $DA_0$=L3', and the distance from vertex B to vertex $M_4$ be $BM_4$=L4'. Thus, the aforementioned formula (2) can be simplified into formula (3):

$$\sum M_{A0} = (G_1 * L1 + G_3 * L3 + G_4 * L4) * \sin\theta_2 + (G_2 * L2' + G_3 * L3' + G_4 * L4') * \sin\theta_3$$

Since both ($G_1$*L1+$G_3$*L3+$G_4$*L4) and ($G_2$*L2'+$G_3$*L3'+$G_4$*L4') are known quantities, the gravity moment of the parallelogram mechanism 3 on vertex A0 is a sinusoidal function associated with the variables $\theta_2$、$\theta_3$.

Based on the aforementioned formula (3), the inventors of the present disclosure have noticed that the variable $\theta_2$ is associated with changes of the gravity moment of the parallelogram mechanism 3 in the first degree of freedom (i.e., the degree of freedom coming from the overall rotation of the parallelogram mechanism 3 relative to the base link 2), and the variable $\theta_3$ is associated with changes of the gravity moment of the parallelogram mechanism 3 in the second degree of freedom (i.e., the degree of freedom coming from relative rotation between the internal linkages of the parallelogram mechanism 3). Therefore, the present disclosure attempts to achieve gravity compensation for the aforementioned first degree of freedom and/or second degree of freedom through reasonable arrangement of one or more rotating components, so as to realize a lighter operation of the mechanical arm 1 in the compensated degree(s) of freedom.

Figure 10:
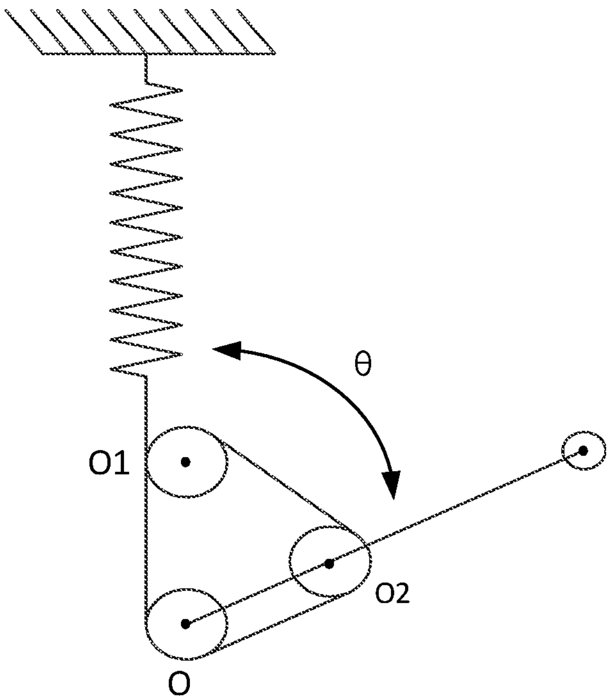
FIG. 10 is a schematic view of the principle of gravity compensation for the parallelogram mechanism by the gravity compensation mechanism according to the present disclosure.
Figure 11:
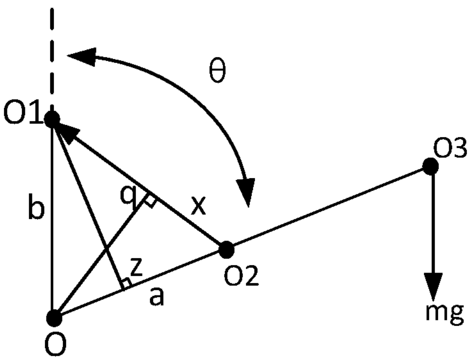
FIG. 11 is a schematic view of the principle of force analysis of the structure of FIG. 10.

Referring to FIGS. 10 and 11, three rotating components are respectively arranged at points O, O1, and O2. The positions of points O and O1 are fixed, while the linkage between points O and O2 can rotate about point O by a variable θ, thus changing the position of point O2. Assuming that the first end of the elastic mechanism is fixedly set, the first end of the cable is fixed to the rotating component at point O1, the second end of the cable is sequentially wound around the rotating component at point O2, guided by the rotating component at point O, and connected to the second end of the elastic mechanism, while the first end of the elastic mechanism is relatively fixedly provided. Typically, assuming that point O3 is the center of gravity (position) of the linkage (i.e., the linkage between points O and O2), let the distance between points O and O1 be b, the distance between points O and O2 be a, and the distance between points O and O3 be 1. Since the length of the cable between points O1 and O2 is a variable equal to the change of the elastic mechanism, let the current length of the cable between points O1 and O2 be x, the initial length be x0, and the mass of the linkage be m. Meanwhile, let the distance from point O to the cable between points O1 and O2 be q, and the distance from point O1 to the linkage between points O and O2 be z.

It is worth noting that in FIGS. 10 and/or 11, the linkage between points O and O2 can represent any other mechanism, such as the parallelogram mechanism 3 according to the present disclosure. Furthermore, the variable θ can represent the angle corresponding to any degree of freedom, such as the first degree of freedom (i.e., associated with the variable $\theta_2$) and/or the second degree of freedom (i.e., associated with the variable $\theta_3$) of the parallelogram mechanism 3 according to the present disclosure.

Furthermore, assume that there is an elastic element with stiffness k that can balance the linkage between points O and O2 at any position, take the linkage as the research object, and the moment equilibrium equation is established at point O as formula (4):

$$\sum M_o = mgl\sin\theta - k(x - x_0)q = 0$$

Assuming $x_0=0$, substituting $x_0=O$ into formula (4), the following formula (5) can be obtained:

$$mgl \sin \theta = kxq$$

From the formula for equal triangle areas (6):

$$qx=az$$

And from the sine function, we know formula (7):

$$z=b \sin \theta$$

Substituting formulas (6) and (7) into formula (5), formula (8) can be obtained:

$$mgl \sin 0=kab \sin \theta$$

Based on the aforementioned formula (8), it can be seen that the compensation for the gravity moment is independent of the variable θ. Therefore, it is clear that the present disclosure can achieve gravity compensation in the aforementioned first degree of freedom and/or the second degree of freedom through reasonable arrangement of one or more rotating components.

In some embodiments according to the present disclosure, when performing gravity compensation in the first degree of freedom (i.e., the degree of freedom associated with the variable $\theta_2$) associated with the parallelogram mechanism 3, the first rotating mechanism 41 and/or the first elastic mechanism 42 can be configured according to formula (9) obtained by associating formula (3) and formula (8):

$$(G_2 * L1 + G_3 * L3 + G_4 * L4) * \sin\theta_2 = k1 * a1 * b1 * \sin\theta_2$$

Wherein k1 represents the elastic coefficient of the first elastic element 421, a1 represents the distance between the rotation axis of the fourth rotating component 414 and the rotation axis of the third rotating component 413, and b1 represents the distance from the rotation axis of the third rotating component 413 to the rotation axis of the second rotating component 412. With such configuration, gravity balance can be achieved at any position (i.e., angle) in the first degree of freedom.

Exemplarily, assuming that k1 and a1 are known and b1 is to be determined, b1 can be determined according to the above formula (9).

Exemplarily, assuming that k1 is known and a1 and b1 are to be determined, a1 and b1 can be determined according to the above formula (9). For instance, a1 and b1 can be determined using methods such as least squares or traversal in combination with the aforementioned formula (9).

Exemplarily, assuming that k1, a1, and b1 are to be determined, k1, a1, and b1 can be determined according to the aforementioned formula (9). For instance, a specific relationship such as a1=b1 can be established between a1 and b1 or k1, and k1, a1, and b1 can be determined using methods such as least squares or traversal in combination with the aforementioned formula (9). In some embodiments according to the present disclosure, when performing gravity compensation in the second degree of freedom (i.e., the degree of freedom associated with the variable $\theta_3$) associated with the parallelogram mechanism 3, the second rotating mechanism 43 and/or the second elastic mechanism 44 can be configured according to formula (10) obtained by associating formula (3) and formula (8):

$$(G_2 * L2' + G_3 * L3' + G_4 * L4') * \sin\theta_3 = k2 * a2 * b2 * \sin\theta_3$$

Wherein k2 represents the elastic coefficient of the second elastic element 441, a2 represents the distance from the rotation axis of the eighth rotating component 434 to the first rotation axis 35, and b2 represents the distance from the rotation axis of the seventh rotating component 433 to the rotation axis of the fifth rotating component 431. With such configuration, gravity balance can be achieved at any position (i.e., angle) in the second degree of freedom.

Exemplarily, assuming that k2 and a2 are known and b2 is to be determined, b2 can be determined according to the aforementioned formula (10).

Exemplarily, assuming that k2 is known and a2 and b2 are to be determined, a2 and b2 can be determined according to the aforementioned formula (10). For instance, a2 and b2 can be determined using methods such as least squares or traversal in combination with the aforementioned formula (10).

Exemplarily, assuming that k2, a2, and b2 are to be determined, k2, a2, and b2 can be determined according to the aforementioned formula (10). For instance, a specific relationship such as a2=b2 can be established between a2 and b2 or k2, and k2, a2, and b2 can be determined using methods such as least squares or traversal in combination with the above formula (10). In some embodiments according to the present disclosure, when performing gravity compensation in both the first degree of freedom (i.e., the degree of freedom associated with the variable $\theta_2$) and the second degree of freedom (i.e., the degree of freedom associated with the variable $\theta_3$) associated with the parallelogram mechanism 3, the first rotating mechanism 41, the first elastic mechanism 42, the second rotating mechanism 43, and/or the second elastic mechanism 44 can be configured according to formula (11) obtained by associating formula (3) and formula (8):

$$(G_1*L1+G_3*L3+G_4*L4)*\sin\theta_2+(G_2*L2'+G_3*L3'+G_4*L4')*\sin\theta_3=k1*a1*b1*\sin\theta_2+k2*a2*b2*\sin\theta_3$$

With such configuration, gravity balance can be achieved at any position (i.e., angle) in both the first and second degrees of freedom. This can effectively prevent the mechanical arm 1, which uses an active method for gravity compensation, from falling in the first or the second degree of freedom when power is lost.

In some embodiments according to the present disclosure, the gravity compensation mechanism 4 may be configured to generate a moment slightly less than the gravity moment of the parallelogram mechanism 3 in the aforementioned first degree of freedom, ensuring that the first linkage 31 remains parallel to the direction of gravity in the absence of external force. For instance, the first rotating mechanism 41 and/or the first elastic mechanism 42 can be configured according to the following formula (12).

$$(G_2*L1+G_3*L3+G_4*L4)*\sin\theta_2>k1*a1*b1*\sin\theta_2$$

In some embodiments according to the present disclosure, the gravity compensation mechanism 4 may be configured to generate a moment slightly greater than the gravity moment of the parallelogram mechanism 3 in the aforementioned second degree of freedom, ensuring that the second linkage 32 tightens upward and the entire parallelogram mechanism is in a collapsed state in the absence of external force. The second rotating mechanism 43 and/or the second elastic mechanism 44 can be configured according to the following formula (13).

$$(G_2*L2'+G_3*L3'+G_4*L4')*\sin\theta_3<k2*a2*b2*\sin\theta_3$$

In some embodiments, the gravity compensation mechanism 4 may further include a first motor. The first motor is coupled to the first linkage 31, for example, the first motor can be provided within the first linkage 31. The first motor can be controlled by a controller to drive the overall rotation of the parallelogram mechanism 3 about the first rotation axis 35. Meanwhile, the first motor can be controlled to generate the compensation moment balanced with the gravity moment in the degree of freedom coming from the overall rotation of the parallelogram mechanism 3 about the first rotation axis 35. In the degree of freedom coming from the overall rotation of the parallelogram mechanism 3 about the first rotation axis 35, the first motor can be used solely to actively compensate the gravity moment, or it can be used in conjunction with the first elastic mechanism 42 and the first rotating mechanism 41 for both active and passive compensation.

In some embodiments, the gravity compensation mechanism 4 may further comprise a second motor. The second motor is coupled to the second linkage 32, for example, the second motor can be provided within the second linkage 32. The second motor can be controlled by the controller to drive the relative rotation between adjacent linkages of the parallelogram mechanism 3. Meanwhile, the second motor can be controlled to generate the compensation moment balanced with the gravity moment in the degree of freedom coming from the relative rotation between adjacent linkages of the parallelogram mechanism 3. In the degree of freedom coming from the relative rotation between adjacent linkages of the parallelogram mechanism 3, the second motor can be used solely to actively compensate the gravity moment, or it can be used in conjunction with the second clastic mechanism 44 and the second rotating mechanism 43 for both active and passive compensation.

In some embodiments, the first clastic mechanism 42 and/or the first rotating mechanism 41, configured according to aforementioned formula (10), can typically be permanently configured and used. However, in other embodiments, the first elastic mechanism 42 and/or the first rotating mechanism 41, configured according to aforementioned formula (10), can be configured more flexibly to facilitate adjustment. In particular, the configuration associated with the first rotating mechanism 41 can be more flexibly configured to be suitable for different scenarios. Taking the first rotating mechanism 41 as an example, it can be configured for easy adjustment of the distance a1 between the rotation axis of the fourth rotating component 414 and the rotation axis of the third rotating component 413, and/or for easy adjustment of the distance b1 between the rotation axis of the third rotating component 413 and the rotation axis of the second rotating component 412.

For example, the fourth rotating component 414 can be provided at an adjustable position on the first linkage 31 for the adjustment of distance a1. Exemplarily, referring to FIG. 12, the gravity compensation mechanism 4 may further include a first guiding component 461 and a first mounting component. The first guiding component 461 is provided on the first linkage 31, the first mounting component is movably provided in the first guiding component 461, and the fourth rotating component 414 is rotatably mounted on the first mounting component, so that the adjustment of distance a1 can be achieved through movement of the fourth rotating component 414 with the first mounting component in the first guiding component 461. Such movement can be implemented manually or automatically.

Taking the movement of the fourth rotating component 414 being automatically implemented as an example, the gravity compensation mechanism 4 may further incorporate a first driving mechanism. The first driving mechanism is coupled to the first guiding component 461 or the first mounting component to drive the first mounting component to move in the first guiding component 461, thereby driving the fourth rotating component 414 to move relative to the first linkage 31.

Figure 12:
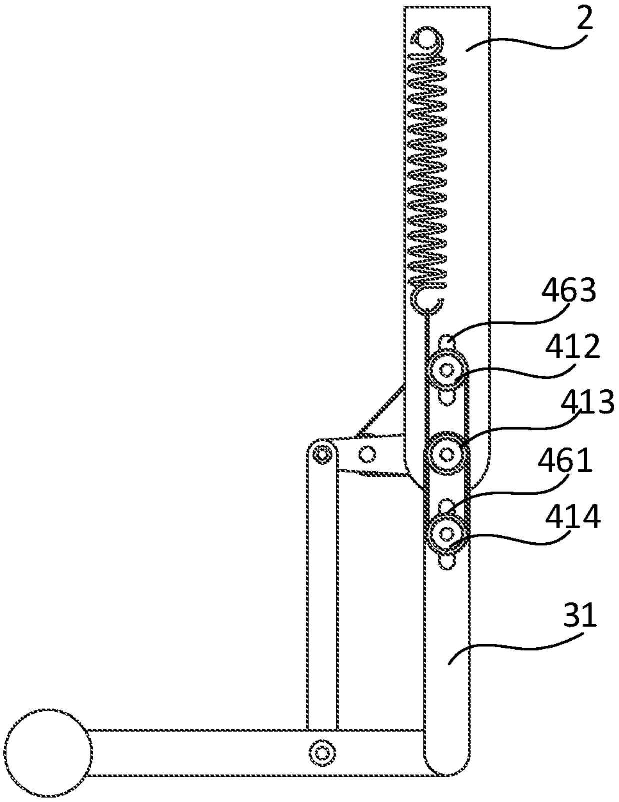
FIG. 12 is a schematic view of a mechanical arm according to yet another embodiment of the present disclosure.

For another example, referring to FIG. 12, the coaxially arranged first rotating component 411 and second rotating component 412 can be provided at an adjustable position on the base link 2 for the adjustment of distance b1. Exemplarily, the gravity compensation mechanism 4 may further comprise a second guiding component 463 and a second mounting component. The second guiding component 463 is provided on the base link 2, and the second mounting component is movably provided in the second guiding component 463. Typically, the first rotating component 411 is fixedly (i.e., non-rotatably) mounted on the second mounting component, while the second rotating component 412 is rotatably mounted on the second mounting component. Therefore, the adjustment of distance b1 can be achieved through the synchronous movement of the first component 411 and second rotating component 412 with the second mounting component in the second guiding component 463. Such movement can be implemented manually or automatically.

Taking the movement of the first component 411 and second rotating component 412 being automatically implemented as an example, the gravity compensation mechanism 4 may further comprise a second driving mechanism. The second driving mechanism is coupled to the second guiding component 463 or the second mounting component to drive the second mounting component to move in the second guiding component 463, thereby driving the first component 411 and second rotating component 412 to move relative to the base link 2.

In the aforementioned embodiments, for example, in the embodiment where the position of the rotating component is adjusted manually, the first guiding component 461 and/or the second guiding component 463 may include a slide rail and/or a slide groove. For instance, the slide groove or the slide rail can be provided along the length of the corresponding first linkage 31 and/or the base link 2.

When considering the weight and center of gravity of the first linkage 31, the influence of the first guiding component 461 on the first linkage 31 can be considered, especially when the first guiding component 461 has a significant influence on the weight and center of gravity of the first linkage 31. Due to the first guiding component 461 and the first linkage 31 being relatively fixed, adjusting only the fourth rotating component 414, whose weight is almost negligible compared to the linkages, does not adversely affect the desired passive gravity compensation.

The elastic coefficient k1 of the first elastic mechanism 42 can also be configured to be adjustable, either alone or in combination. For instance, the first elastic mechanism 42 may include a variable-stiffness spring to achieve adjustment of the elastic coefficient k1. Alternatively, the first elastic mechanism 42 can typically be selected from conventional tension springs or compression springs, and the adjustment of the elastic coefficient k1 is mainly achieved by adjusting the distances a1 and/or b1.

In some embodiments, the second elastic mechanism 44 and/or the second rotating mechanism 43, configured according to the aforementioned formula (11), can typically be permanently configured and used. However, in other embodiments, the second clastic mechanism 44 and/or the second rotating mechanism 43 configured according to the aforementioned formula (11), can be configured in a more flexible manner to facilitate adjustment. In particular, the configuration associated with the second rotating mechanism 43 can be more flexibly configured to be suitable for different scenarios. Taking the second rotating mechanism 43 as an example, it can be configured for easy adjustment of the distance a2 between the rotation axis of the eighth rotating component 434 and the rotation axis of the seventh rotating component 433, and/or for easy adjustment of the distance b2 between the rotation axis of the seventh rotating component 433 and the rotation axis of the fifth rotating component 431.

Figure 13:
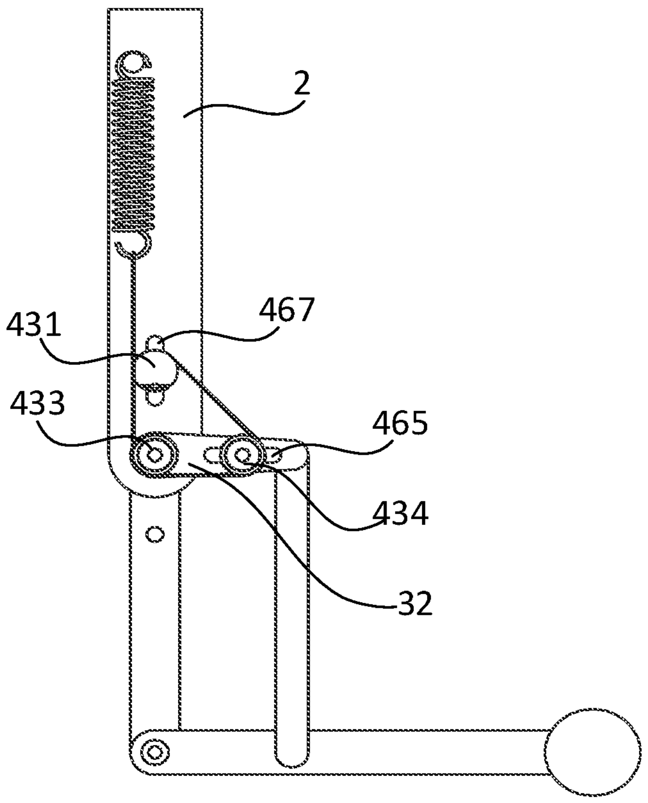
FIG. 13 is a schematic view of a mechanical arm according to yet another embodiment of the present disclosure.

For instance, the eighth rotating component 434 can be provided at an adjustable position on the second linkage 32 for the adjustment of distance a2. Exemplarily, referring to FIG. 13, the gravity compensation mechanism 4 further includes a third guiding component 465 and a third mounting component. The third guiding component 465 is provided on the second linkage 32, and the third mounting component is movably provided in the third guiding component 465. The eighth rotating component 434 is rotatably mounted on the third mounting component, so that the adjustment of distance a2 can be achieved through movement of the eighth rotating component 434 with the third mounting component in the third guiding component 465. Such movement can be implemented manually or automatically.

Taking the movement of the eighth rotating component 434 being automatically implemented as an example, the gravity compensation mechanism 4 may further include a third driving mechanism coupled to the third guiding component 465 or the third mounting component to drive the movement of the third mounting component on the third guiding component 465, thereby driving the eighth rotating component 434 to move relative to the second linkage 32.

For another example, the fifth rotating component 431 can be provided at an adjustable position on the base link 2 for the adjustment of distance b2. Exemplarily, referring again to FIG. 13, the gravity compensation mechanism 4 further includes a fourth guiding component 467 and a fourth mounting component. The fourth guiding component 467 is provided on the base link 2, and the fourth mounting component is movably provided on the fourth guiding component 467. Typically, the fifth rotating component 431 is fixedly (i.e., non-rotatably) mounted on the fourth mounting component. When the aforementioned sixth rotating component 432 coaxially disposed with the fifth rotating component is included, the sixth rotating component 432 is rotatably mounted on the fourth mounting component. Therefore, the adjustment of distance b2 can be achieved through the synchronous movement of the fifth rotating component 431 (and the sixth rotating component 432) with the fourth mounting component in the fourth guiding component 467. Such movement can be implemented manually or automatically.

Taking the movement of the fifth rotating component 431 being automatically implemented as an example, the gravity compensation mechanism 4 may further include a fourth driving mechanism coupled to the fourth guiding component 467 or the fourth mounting component to drive the movement of the fourth mounting component in the fourth guiding component 467, thereby driving the fifth rotating component 431 to move relative to the base link 2. Naturally, when a sixth rotating component 432 is provided on the fourth mounting component, the sixth rotating component 432 also moves with the fourth mounting component.

In the aforementioned embodiments, for example, in embodiments where the position of the corresponding rotating component is adjusted manually, the third guiding component 465 and/or the fourth guiding component 467 may include a slide rail and/or a slide groove. Exemplarily, the slide groove or the slide rail can be disposed along the length of the corresponding second linkage 32 and/or base link 2. When considering the weight and center of gravity of the second linkage 32, the influence of the third guiding component 465 on the second linkage 32 can be considered, especially when the third guiding component 465 has an influence on the weight and center of gravity of the second linkage 32. Due to the third guiding component 465 and the second linkage 32 being relatively fixed, adjusting only the fourth rotating component 414, whose weight is almost negligible compared to the linkages, does not adversely affect the desired passive gravity compensation.

The elastic coefficient k2 of the second elastic mechanism 44 can also be configured adjustable, either alone or in combination. For instance, the second elastic mechanism 44 may include a variable stiffness spring to achieve adjustment of the elastic coefficient k2. Alternatively, the second elastic mechanism 44 can typically be selected from conventional tension springs or compression springs, and the adjustment of the elastic coefficient k2 is mainly achieved by adjusting the distances a2 and/or b2.

The corresponding configurations of the aforementioned first driving mechanism and/or the second driving mechanism can be effectively applied to adapt to change of the load 5 connected to the distal end of the parallelogram mechanism 3, providing better gravity compensation for the parallelogram mechanism 3.

In the aforementioned embodiments, for example, in the embodiment where the position of the corresponding rotating component is adjusted automatically, each driving mechanism can be implemented by means of a linear motor, a ball screw pair, rack and pinion, etc.

For instance, when the first driving mechanism, the second driving mechanism, the third driving mechanism, and/or the fourth driving mechanism comprise(s) a linear motor, the stator of the linear motor serves as a guiding component, the mover of the linear motor serves as a mounting component, and the linear motor serves as the guiding component, the mounting component, and the driving mechanism simultaneously.

For another example, when the first driving mechanism, the second driving mechanism, the third driving mechanism, and/or the fourth driving mechanism comprise(s) a ball screw pair, the screw of the ball screw pair serves as a guiding component, the slider of the ball screw pair serves as a mounting component. Naturally, the ball screw pair further includes a motor coupled to the screw to move the slider on the screw by driving the screw to rotate. The ball screw pair serves as the guiding component, the mounting component, and the driving mechanism concurrently.

Figure 14:
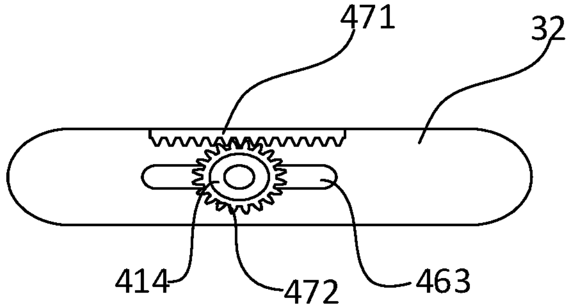
FIG. 14 is a partial schematic view of a mechanical arm according to yet another embodiment of the present disclosure.

For yet another example, when the first driving mechanism, the second driving mechanism, the third driving mechanism, and/or the fourth driving mechanism comprise(s) rack and pinion, a slide groove can be provided on the corresponding linkage as the guiding component, and a rack parallel to the slide groove or a slide rail is provided on the corresponding linkage. The pinion is movably provided in the slide groove and engages with the rack. The rotating component is rotatably provided on the gear, and the rotation of the rotating component is independent of the rotation of the gear. The pinion can be driven by a motor to rotate so that the pinion can move in the slide groove. In this embodiment, the rack and pinion serves as both the mounting component and the driving mechanism. Taking the linkage being the second linkage 32 as an example, referring to FIG. 14, the slide groove serving as the guiding component 463 is disposed on the second linkage 32. In the rack and pinion of the second driving mechanism, the rack 471 is disposed on the second linkage 32 in parallel with the slide groove 463, and the pinion 472 provided with the fourth rotating component 414 is movably disposed in the slide groove 463 and engages with the rack 471.

In the aforementioned embodiments, each driving mechanism (the first driving mechanism, the second driving mechanism, the third driving mechanism, and/or the fourth driving mechanism) can be driven by one or more controller to adjust corresponding distances (a1, b1, a2, and/or b2). This can correct issues caused by assembly errors or change of the load 5. For instance, corrections can be made when there are static changes in the structure of the load 5, or real-time corrections can be performed when there are dynamic changes in the state of the load 5, thereby achieving a better gravity balancing effect.

In some embodiments, the diameters of the multiple rotating components in the first rotating mechanism 41 are the same. For instance, the diameters of the first rotating component 411, the second rotating component 412, the third rotating component 413, and the fourth rotating component 414 are the same.

In some embodiments, the diameters of the multiple rotating components in the second rotating mechanism 43 are the same. For instance, the diameters of the fifth rotating component 431, the seventh rotating component 433, and the eighth rotating component 434 are the same. Naturally, when the sixth rotating component 432 is included in the second rotating mechanism 43, the diameter of the sixth rotating component 432 should be the same as the diameters of the other rotating components.

In some embodiments, the angle range of the rotation between two adjacent linkages in the parallelogram mechanism 3 is 0 € (0°, 180°), that is, the angle of rotation between two adjacent linkages (such as the first linkage 31 and the second linkage 32) cannot reach 0° or 180° to avoid reaching a singular point (which includes the singular points of 0° and) 180° that would prevent gravity compensation in the second degree of freedom.

The present disclosure also provides an installation method for a mechanical arm, comprising:

- a step of providing a base link;
- a step of providing a parallelogram mechanism comprising a first linkage, a second linkage, a third linkage, and a fourth linkage sequentially connected by rotation, and rotatably connecting the parallelogram mechanism to the base link, wherein an axis about which the parallelogram mechanism rotates relative to the base link typically coincides with a first rotation axis between the first linkage and the second linkage;
- a step of providing a rotating mechanism and an elastic mechanism, coupling the rotating mechanism to the base link and at least one of the first linkage and the second linkage, and coupling the elastic mechanism to the base link and the rotating mechanism According to the above-mentioned steps, a compensation moment balanced with a gravity moment of the parallelogram mechanism can be generated in a degree of freedom associated with the parallelogram mechanism.

In some embodiments, the rotating mechanism comprises a first rotating mechanism, and the elastic mechanism comprises a first elastic mechanism, and the step of coupling the rotating mechanism to the base link and at least one of the first linkage and the second linkage, and coupling the elastic mechanism to the base link and the rotating mechanism comprises:

a step of coupling the first rotating mechanism to the base link and one of the first linkage and the second linkage, and coupling the first elastic mechanism to the base link and the first rotating mechanism to generate the compensation moment balanced with the gravity moment of the parallelogram mechanism in one degree of freedom associated with the parallelogram mechanism.

In some embodiments, the rotating mechanism comprises a second rotating mechanism, and the clastic mechanism comprises a second elastic mechanism, and the step of distributing the rotating mechanism to at least one of the first linkage and the second linkage and to the base link, and coupling the elastic mechanism to the base link and the rotating mechanism comprises:

a step of coupling the second rotating mechanism to the base link and the other of the first linkage and the second linkage, and coupling the second elastic mechanism to the base link and the second rotating mechanism to generate the compensation moment balanced with the gravity moment of the parallelogram mechanism in another degree of freedom associated with the parallelogram mechanism.

In some embodiments, the parallelogram mechanism comprises a first degree of freedom, the first degree of freedom comprises the degree of freedom coming from the overall rotation of the parallelogram mechanism about the first rotation axis. The step of coupling the first rotating mechanism to the base link and one of the first linkage and the second linkage comprises:

a step of distributing the first rotating mechanism on the base link and the first linkage, thereby enabling the first elastic mechanism to generate the compensation moment balanced with the gravity moment of the parallelogram mechanism in the first degree of freedom.

In some embodiments, the first rotating mechanism comprises a first rotating component, a second rotating component, a third rotating component, and a fourth rotating component, and the first elastic mechanism comprises a first elastic element and a first cable. The step of coupling the first rotating mechanism to the base link and one of the first linkage and the second linkage, and coupling the first elastic mechanism to the base link and the first rotating mechanism comprises:

a step of fixedly connecting the first rotating component to the base link, coaxially arranging the second rotating component with the first rotating component such that the second rotating component is rotatable relative to the first rotating component, and rotatably connecting the third rotating component and the fourth rotating component to the first linkage.

Typically, the rotation axis of the third rotating component coincides with the first rotation axis, and the rotation axes of the second rotating component and the fourth rotating component are parallel to the first rotation axis.

The installation method further comprises a step comprising: connecting a first end of the first elastic element to the base link, fixing a first end of the first cable to the first rotating component, winding the first cable around the second rotating component, guiding the first cable through the third rotating component, winding the first cable around the fourth rotating component, and then connecting a second end of the first cable to a second end of the first elastic element.

In a preferred embodiment, the installation method further comprises:

a step of configuring the first elastic element and the first rotating mechanism according to the following formula:

$$k1 \times a1 \times b1 = G1 \times L1 + G3 \times L3 + G4 \times L4$$

In the formula, k1 represents the elastic coefficient of the first elastic element, a1 represents the distance from the rotation axis of the fourth rotating component to the first rotation axis, b1 represents the distance from the rotation axis of the third rotating component to the rotation axis of the second rotating component, G1 represents the gravity of a first linkage, G3 represents the gravity of a third linkage, G4 represents the gravity of a fourth linkage, L1 represents the distance from the center of gravity of the first linkage to the first rotation axis, L3 represents the distance from the center of gravity of the third linkage to a second rotation axis between the second linkage and the third linkage, and L4 represents the distance from a fourth rotation axis between the fourth linkage and the first linkage to the first rotation axis.

In some embodiments, the parallelogram mechanism comprises a second degree of freedom, the second degree of freedom comprises the degree of freedom coming from the relative rotation between the two adjacent linkages of the parallelogram mechanism. The step of coupling the second rotating mechanism to the base link and another one of the first linkage and the second linkage, and coupling the second elastic mechanism to the base link and the second rotating mechanism comprises:

a step of distributing the second rotating mechanism on the base link and the second linkage, thereby enabling the second elastic mechanism to generate the compensation moment balanced with the gravity moment of the parallelogram mechanism in the second degree of freedom.

In some embodiments, the second rotating mechanism comprises a fifth rotating component, a seventh rotating component, and an eighth rotating component, and the second elastic mechanism comprises a second elastic element and a second cable. The step of coupling the second rotating mechanism to the base link and another one of the first linkage and the second linkage, and coupling the second elastic mechanism to the base link and the second rotating mechanism, comprises:

a step of fixing the fifth rotating component to the base link, and rotatably connecting the seventh rotating component and the eighth rotating component to the second linkage.

Typically, the rotation axis of the seventh rotating component coincides with the first rotation axis, and the rotation axis of the eighth rotating component is parallel to the first rotation axis.

The installation method further comprises a step comprising: connecting a first end of the second elastic element to the base link, fixing a first end of the second cable to the fifth rotating component, guiding the second cable through the seventh rotating component, winding the second cable around the eighth rotating component, and connecting a second end of the second cable to a second end of the second elastic element.

In a preferred embodiment, the installation method further comprises:

a step of configuring the second elastic element and the second rotating mechanism according to the following formula:

$$k2 \times a2 \times b2 = G2 \times L2' + G3 \times L3' + G4 \times L4'$$

In the formula, k2 represents the elastic coefficient of the second elastic element, a2 represents the distance from the rotation axis of the eighth rotating component to the first rotation axis, b2 represents the distance from the rotation axis of the seventh rotating component to the rotation axis of the fifth rotating component, G2 represents the gravity of a second linkage, G3 represents the gravity of a third linkage, G4 represents the gravity of a fourth linkage, L2' represents the distance from the center of gravity of the second linkage to the first rotation axis, L3' represents the distance from a second rotation axis between the second linkage and the third linkage to the first rotation axis, and L4' represents the distance from the center of gravity of the fourth linkage to a fourth rotation axis between the fourth linkage and the first linkage.

The mechanical arm comprising the base link, parallelogram mechanism, and gravity compensation mechanism described in the present disclosure is suitable for use in robots across multiple technical fields, and can be used as at least a portion of such robots. For instance, the mechanical arm of the present disclosure can be used as at least a portion of the mechanical arm of a surgical robot in the medical field. Alternatively, the mechanical arm of the present disclosure can be used as at least a portion of the mechanical arm of an industrial robot in the industrial field.

In some embodiments, the present disclosure also provides a surgical robot comprising a master operating platform 100 and a slave operating equipment controlled by the master operating platform 100. The master operating platform 100 has an operating portion 110, and a doctor can send a control command including a pose instruction to the slave operating equipment by operating (e.g., dragging) the operating portion 110 to execute the control command.

The operating portion 110 comprises a mechanical arm. The mechanical arm 110 comprises a base link 2', and further comprises a parallelogram mechanism 3' having a first linkage 31', a second linkage 32', a third linkage 33', and a fourth linkage 34' that are sequentially connected by rotation. The mechanical arm also comprises a gravity compensation mechanism (not shown in figure) coupled between the base link 2' and the parallelogram mechanism 3'. Since the basic components of the mechanical arm, namely the base link 2' and the parallelogram mechanism 3', are respectively equivalent to the base link 2 and the parallelogram mechanism 3 of the mechanical arm 1 according to any one of the above-mentioned embodiments, the configuration of the gravity compensation mechanism of the mechanical arm 110 can be implemented by referring to the configuration of the gravity compensation mechanism 4 of the mechanical arm 1 according to any one of the above-mentioned embodiments, and details will not be repeated here.

Figure 16:
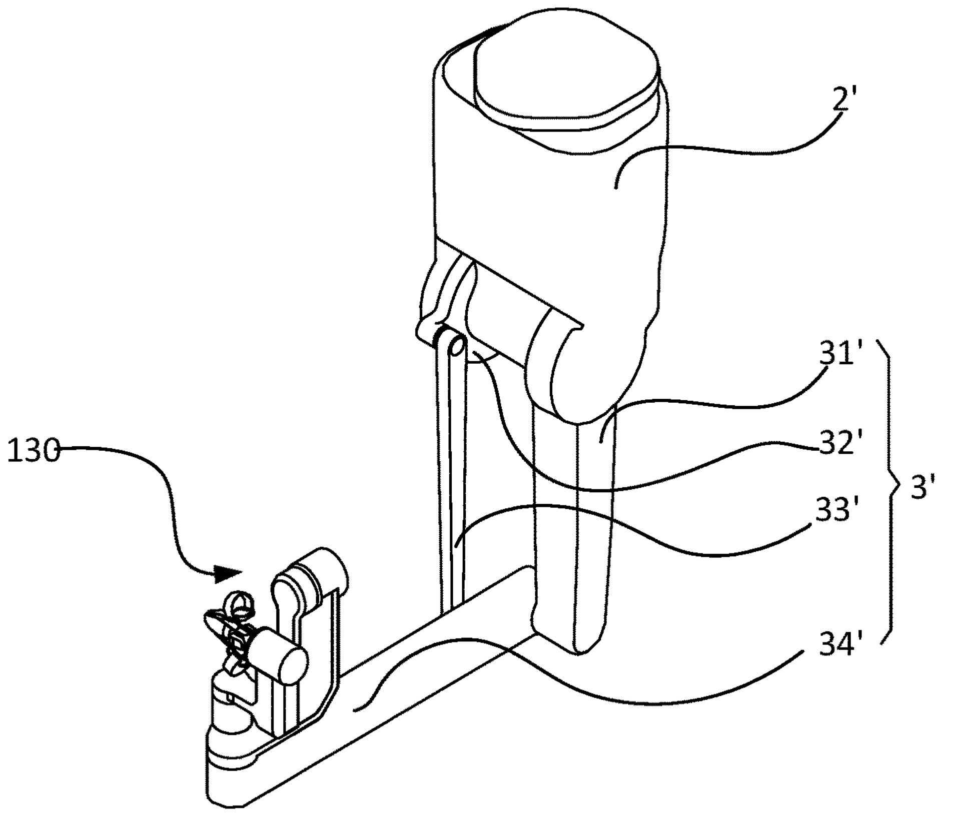
FIG. 16 is an enlarged view of the operating portion of FIG. 15.

In some embodiments, referring to FIG. 16, the parallelogram mechanism 3' of the mechanical arm 110 can further include a load 130 at its distal end. Specifically, the load 130 can be disposed at the distal end of the fourth linkage 34'. The load 130 can be referred to as a wrist mechanism, and the wrist mechanism 130 has multiple degrees of freedom to generate the control command including position and/or orientation for controlling the motion of the slave operating equipment in coordination with the base link 2' and the parallelogram mechanism 3'. In some embodiments, the wrist mechanism 130 can have an additional degree of freedom for controlling the opening and closing of an end effector mounted on the slave operating equipment.

Figure 15:
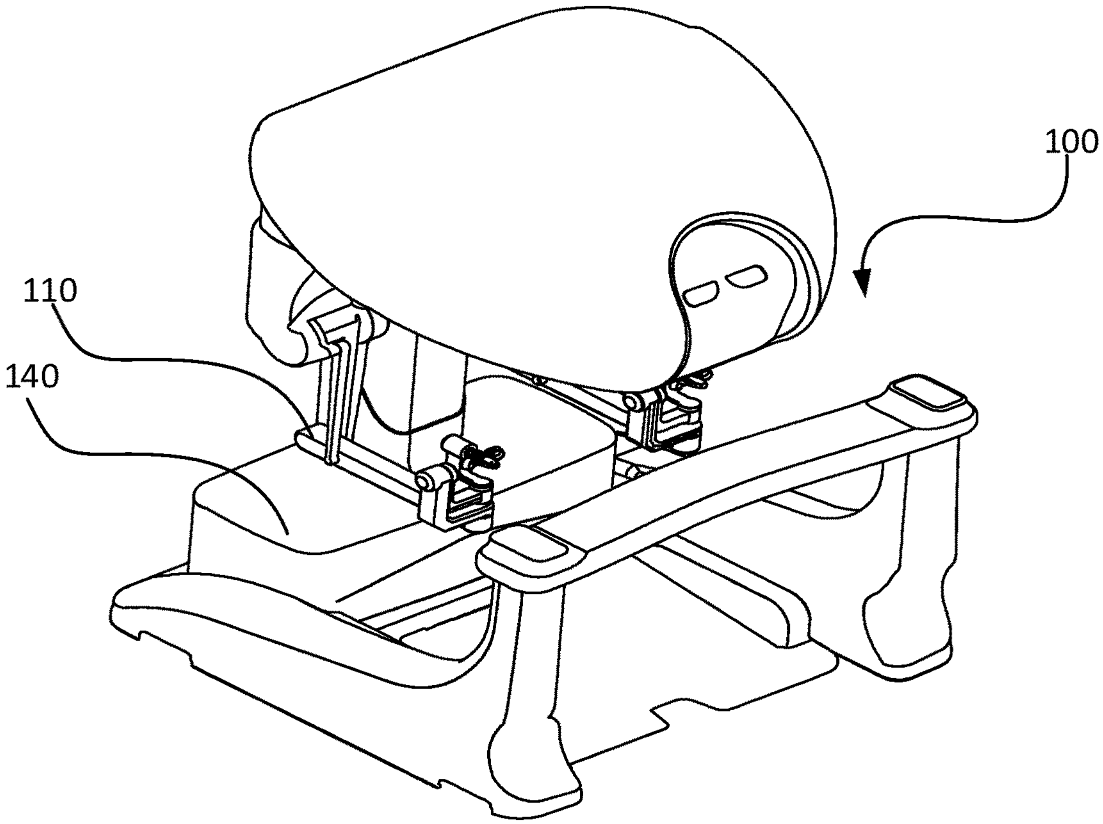
FIG. 15 is a schematic view of a master operating platform according to an embodiment of the present disclosure.

In some embodiments, referring to FIG. 15, the master operating platform 100 can include a base 140, and the base link 2' can be rotatably coupled to the base 140.

By coupling the gravity compensation mechanism between the base link 2' and the parallelogram mechanism 3', the present disclosure can effectively balance the gravity moment of the parallelogram mechanism 3'. Since the present disclosure differs from the related art in which a counterweight compensation method is used, it effectively improves the doctor's operating feel, i.e., improves force transparency. Furthermore, since the present disclosure differs from the related art in which an active compensation method is used, there is no need to worry about the mechanical arm falling when power is lost, and it helps to save electricity.

When understanding the "load" described in the present disclosure, the wrist mechanism 130 shown in FIG. 16 can be used as a specific example to aid in understanding.

The technical features of the above-mentioned embodiments can be combined in any manner. To simplify the description, not all possible combinations of the technical features in the above-mentioned embodiments are described. However, as long as the combinations of these technical features do not contradict each other, they should all be considered as falling within the scope described in this specification.

The above-mentioned embodiments only express several implementation modes of the present disclosure, and the description is relatively specific and detailed, but they cannot be understood as limiting the scope of the patent application. It should be noted that for one skilled in the art, without departing from the concept of the present disclosure, several modifications and improvements can be made, and these all belong to the protection scope of the present disclosure. Therefore, the protection scope of the patent of the present disclosure should be subject to the appended claims.

What is claimed is:

1. A mechanical arm, comprising:

a base link;

a parallelogram mechanism, comprising a first linkage, a second linkage, a third linkage, and a fourth linkage sequentially connected by rotation, wherein the parallelogram mechanism is rotatably connected to the base link about an axis coinciding with a first rotation axis between the first linkage and the second linkage, and the parallelogram mechanism has a degree of freedom coming from an overall rotation of the parallelogram mechanism relative to the base link and a degree of freedom coming from relative rotation between two adjacent linkages of the parallelogram mechanism; and a gravity compensation mechanism, comprising a rotating mechanism and an elastic mechanism, wherein the rotating mechanism comprises a first rotating mechanism, the first rotating mechanism is coupled to the base link and at least one of the first linkage and the second linkage, the elastic mechanism comprises a first elastic mechanism, the first elastic mechanism comprises a first elastic element and a first cable, one end of the first elastic element is connected to the base link, and an other end of the first elastic element is coupled to the rotating mechanism via the first cable, so as to generate a compensation moment balanced with a gravity moment of the parallelogram mechanism in at least one degree of freedom associated with the parallelogram mechanism.

2. The mechanical arm of claim 1, wherein the rotating mechanism comprises a second rotating mechanism, the elastic mechanism comprises a second elastic mechanism, the second rotating mechanism is coupled to the base link and the other of the first linkage and the second linkage, the second elastic mechanism comprises a second elastic element and a second cable, a first end of the second elastic element is connected to the base link, and a second end of the second elastic element is coupled to the rotating mechanism via the second cable, so as to generate the compensation moment balanced with the gravity moment of the parallelogram mechanism in another degree of freedom associated with the parallelogram mechanism.

3. The mechanical arm of claim 2, wherein the parallelogram mechanism comprises a first degree of freedom, the first degree of freedom comprises the degree of freedom coming from the overall rotation of the parallelogram mechanism about the first rotation axis, the first rotating mechanism is coupled to the base link and the first linkage, and the first elastic mechanism generates the compensation moment balanced with the gravity moment of the parallelogram mechanism in the first degree of freedom.

4. The mechanical arm of claim 3, wherein the first rotating mechanism comprises a first rotating component, a second rotating component, a third rotating component and a fourth rotating component, the first rotating component is fixedly connected to the base link, the second rotating component is coaxially provided with the first rotating component and the second rotating component is rotatable with respect to the first rotating component, each of the third rotating component and the fourth rotating component is rotatably connected to the first linkage, a rotation axis of the third rotating component coincides with the first rotation axis, a rotation axis of the second rotating component and a rotation axis of the fourth rotating component are parallel to the first rotation axis;

a first end of the first cable is fixedly connected to the first rotating component, a second end of the first cable is sequentially wound around the second rotating component, guided by the third rotating component, wound around the fourth rotating component and connected to a second end of the first elastic element; or the first end of the first elastic element is connected to the base link, the first end of the first cable is fixedly connected to the first rotating component, the second end of the first cable is sequentially wound around the fourth rotating component, guided by the third rotating component, wound around the second rotating component and connected to the second end of the first elastic element.

5. The mechanical arm of claim 4, wherein an elastic coefficient of the first elastic element, a distance between the rotation axis of the third rotating component and the rotation axis of the second rotating component, and a distance between the rotation axis of the fourth rotating component and the first rotation axis comprise at least one first parameter to be determined, the first parameter to be determined each is determined based on a first condition and a second condition, the first condition comprises gravity of the first linkage, gravity of the third linkage, gravity of the fourth linkage, a distance between a center of gravity of the first linkage and the first rotation axis, a distance from a center of gravity of the third linkage to a second rotation axis between the second linkage and the third linkage, and a distance from a fourth rotation axis between the fourth linkage and the first linkage to the first rotation axis, the second condition comprises parameters other than the first parameter to be determined among the elastic coefficient of the first elastic element, the distance between the rotation axis of the third rotating component and the rotation axis of the second rotating component, and the distance between the rotation axis of the fourth rotating component and the first rotation axis.

6. The mechanical arm of claim 5, wherein a configuration of the first elastic element and the first rotating mechanism satisfies a formula as follows:

$$k1 \times a1 \times b1 \leq G1 \times L1 + G3 \times L3 + G4 \times L4$$

in which k1 represents the elastic coefficient of the first elastic element, a1 represents the distance between the rotation axis of the fourth rotating component and the rotation axis of the third rotating component, b1 represents the distance between the rotation axis of the third rotating component and the rotation axis of the second rotating component, G1 represents the gravity of the first linkage, G3 represents the gravity of the third linkage, G4 represents the gravity of the fourth linkage, L1 represents the distance between the center of gravity of the first linkage and the first rotation axis, L3 represents the distance from the center of gravity of the third linkage to the second rotation axis between the second linkage and the third linkage, and L4 represents the distance from the fourth rotation axis between the fourth linkage and the first linkage to the first rotation axis.

7. The mechanical arm of claim 5, wherein an elastic coefficient of the second elastic element, a distance between the rotation axis of the seventh rotating component and the rotation axis of the fifth rotating component, and a distance between the rotation axis of the eighth rotating component and the rotation axis of the seventh rotating component comprise at least one second parameter to be determined, the second parameter to be determined each is determined based on a third condition and a fourth condition, the third condition comprises gravity of the second linkage, gravity of the third linkage, gravity of the fourth linkage, a distance between a center of gravity of the second linkage and the first rotation axis, a distance from a second rotation axis between the second linkage and the third linkage to the first rotation axis, and a distance from a center of gravity of the fourth linkage to a fourth rotation axis between the fourth linkage and the second linkage, the fourth condition comprises parameters other than the second parameter to be determined among the elastic coefficient of the second elastic element, the distance between the rotation axis of the seventh rotating component and the rotation axis of the fifth rotating component, and the distance between the rotation axis of the eighth rotating component and the rotation axis of the seventh rotating component.

8. The mechanical arm of claim 4, wherein the first elastic element comprises a variable-stiffness spring to achieve the elastic coefficient, the distance between the rotation axis of the fourth rotating component and the first rotation axis, and/or the distance between the rotation axis of the third rotating component and the rotation axis of the second rotating component being adjustable.

9. The mechanical arm of claim 4, wherein the gravity compensation mechanism comprises a first guiding component and a first mounting component, the first guiding component is provided on the first linkage, the first mounting component is movably provided in the first guiding component, and the fourth rotating component is rotatably mounted on the first mounting component; and/or the gravity compensation mechanism comprises a second guiding component and a second mounting component, the second guiding component is provided on the base link, the first rotating component is fixedly mounted on the second mounting component, and the second rotating component is rotatably mounted on the second mounting component.

10. The mechanical arm of claim 9, wherein the gravity compensation mechanism further comprises a first driving mechanism coupled to the first guiding component or the first mounting component to drive the first mounting component to move in the first guiding component, thereby driving the fourth rotating component to move relative to the first linkage; and the gravity compensation mechanism further comprises a second driving mechanism coupled to the second guiding component or the second mounting component to drive the second mounting component to move in the second guiding component, thereby driving the first rotating component and the second rotating component to move relative to the base link.

11. The mechanical arm of claim 10, wherein the gravity compensation mechanism further comprises a third driving mechanism coupled to the third guiding component or the third mounting component to drive the third mounting component to move in the third guiding component, thereby driving the eighth rotating component to move relative to the second linkage; and the gravity compensation mechanism further comprises a fourth driving mechanism coupled to the fourth guiding component or the fourth mounting component to drive the fourth mounting component to move in the fourth guiding component, thereby driving the fifth rotating component to move relative to the base link.

12. The mechanical arm of claim 9, wherein the gravity compensation mechanism comprises a third guiding component and a third mounting component, the third guiding component is provided on the second linkage, the third mounting component is movably provided in the third guiding component, and the eighth rotating component is rotatably mounted on the third mounting component; and the gravity compensation mechanism comprises a fourth guiding component and a fourth mounting component, the fourth guiding component is provided on the base link, the fourth mounting component is movably provided on the fourth guiding component, and the fifth rotating component is fixedly mounted on the fourth mounting component.

13. The mechanical arm of claim 2, wherein the parallelogram mechanism comprises a second degree of freedom, the second degree of freedom comprises the degree of freedom coming from the relative rotation between the two adjacent linkages of the parallelogram mechanism, the second rotating mechanism is coupled to the base link and the second linkage, and the second elastic mechanism generates the compensation moment balanced with the gravity moment of the parallelogram mechanism in the second degree of freedom.

14. The mechanical arm of claim 13, wherein the second rotating mechanism comprises a fifth rotating component, a sixth rotating component, a seventh rotating component, and an eighth rotating component, the fifth rotating component is fixedly connected to the base link, the sixth rotating component is coaxially provided with the fifth rotating component and the sixth rotating component is rotatable with respect to the fifth rotating component, each of the seventh rotating component and the eighth rotating component is rotatably connected to the second linkage, a rotation axis of the seventh rotating component coincides with the first rotation axis, a rotation axis of the fifth rotating component and a rotation axis of the eighth rotating component are parallel to the first rotation axis;

a first end of the second cable is fixedly connected to the fifth rotating component, a second end of the second cable is sequentially guided by the seventh rotating component, wound around the eighth rotating component and connected to a second end of the second elastic element; or the first end of the second elastic element is connected to the base link, the first end of the second cable is fixedly connected to the fifth rotating component, the second end of the second cable is sequentially wound around the eighth rotating component, guided by the seventh rotating component and connected to the second end of the second elastic element.

15. The mechanical arm of claim 14, wherein a configuration of the second elastic element and the second rotating mechanism satisfies a formula as follows:

$$k2 \times a2 \times b2 \geq G2 \times L2' + G3 \times L3' + G4 \times L4'$$

in which k2 represents the elastic coefficient of the second elastic element, a2 represents the distance between the rotation axis of the eighth rotating component and the rotation axis of the seventh rotating component, b2 represents the distance between the rotation axis of the seventh rotating component and the rotation axis of the fifth rotating component, G2 represents the gravity of the second linkage, G3 represents the gravity of the third linkage, G4 represents the gravity of the fourth linkage, L2' represents the distance between the center of gravity of the second linkage and the first rotation axis, L3' represents the distance from the second rotation axis between the second linkage and the third linkage to the first rotation axis, and L4' represents the distance from the center of gravity of the fourth linkage to the fourth rotation axis between the fourth linkage and the second linkage.

16. The mechanical arm of claim 14, wherein the second elastic element comprises a variable-stiffness spring to achieve the elastic coefficient, the distance between the rotation axis of the eighth rotating component and the first rotation axis, and/or the distance between the rotation axis of the seventh rotating component and the rotation axis of the fifth rotating component being adjustable.

17. The mechanical arm of claim 1, wherein the gravity compensation mechanism further comprises a first motor coupled to the first linkage to actively compensate for the gravity moment in the degree of freedom coming from the overall rotation of the parallelogram mechanism about the first rotation axis; and the gravity compensation mechanism further comprises a second motor coupled to the second linkage to actively compensate for the gravity moment in the degree of freedom coming from the relative rotation between the adjacent linkages of the parallelogram mechanism.

18. The mechanical arm of claim 1, wherein an angle range of the rotation between the two adjacent linkages in the parallelogram mechanism is $\theta \in (0°, 180°)$; the parallelogram mechanism comprises a load connected to a distal end of the parallelogram mechanism, and the gravity compensation mechanism is further configured to generate a compensation moment balanced with a gravity moment of the parallelogram mechanism comprising the load.

19. A master operating platform, comprising an operating portion configured to generate a control command which comprises a pose instruction, wherein the operation portion comprises the mechanical arm of claim 1.

20. A surgical robot, comprising a slave operating equipment and the master operating platform of claim 19, wherein the slave operating equipment performs a corresponding operation based on the control command from the master operating platform.

* * * * *